(12) United States Patent
Howe et al.

(10) Patent No.: US 11,815,584 B2
(45) Date of Patent: Nov. 14, 2023

(54) METHOD AND APPARATUS FOR QUASI-DIFFUSION MAGNETIC RESONANCE IMAGING

(71) Applicant: ST GEORGE'S HOSPITAL MEDICAL SCHOOL, Tooting London (GB)

(72) Inventors: Franklyn Arron Howe, Greater London (GB); Thomas Richard Barrick, Greater London (GB); Matthew Hall, London (GB)

(73) Assignee: ST GEORGE'S HOSPITAL MEDICAL SCHOOL, Tooting London (GB)

( * ) Notice: Subject to any disclaimer, the term of this patent is extended or adjusted under 35 U.S.C. 154(b) by 24 days.

(21) Appl. No.: 17/626,084

(22) PCT Filed: Jul. 8, 2020

(86) PCT No.: PCT/GB2020/051639
§ 371 (c)(1),
(2) Date: Jan. 10, 2022

(87) PCT Pub. No.: WO2021/005363
PCT Pub. Date: Jan. 14, 2021

(65) Prior Publication Data
US 2022/0381865 A1    Dec. 1, 2022

(30) Foreign Application Priority Data
Jul. 11, 2019 (GB) ..................... 1909982

(51) Int. Cl.
*G01R 33/563* (2006.01)
*A61B 5/055* (2006.01)
*G01R 33/56* (2006.01)

(52) U.S. Cl.
CPC ........ *G01R 33/56341* (2013.01); *A61B 5/055* (2013.01); *G01R 33/5608* (2013.01)

(58) Field of Classification Search
None
See application file for complete search history.

(56) References Cited

U.S. PATENT DOCUMENTS

| | | | |
|---|---|---|---|
| 2003/0178994 A1 | 9/2003 | Hurlimann et al. | |
| 2011/0137567 A1 | 6/2011 | Li et al. | |
| 2016/0022169 A1* | 1/2016 | Breeuwer | A61B 5/055 600/420 |

FOREIGN PATENT DOCUMENTS

| | | | | |
|---|---|---|---|---|
| DE | 102014204823 A1 * | 2/2015 | ........... | A61B 6/4441 |
| WO | WO-2014138529 A1 | 9/2014 | | |
| WO | WO-2017042280 A1 * | 3/2017 | ............. | A61B 8/085 |

OTHER PUBLICATIONS

Abramson RG, Burton KR, Yu JP, Scalzetti EM, Yankeelov TE, Rosenkrantz AB, Mendiratta-Lala M, Bartholmai BJ, Ganeshan D, Lenchik L, Subramaniam RM (2015). Methods and challenges in quantitative imaging biomarker development. Academic Radiology, 22(1): 25-32.

(Continued)

*Primary Examiner* — Rodney E Fuller
(74) *Attorney, Agent, or Firm* — Harness, Dickey & Pierce, P.L.C.

(57) ABSTRACT

A computer-implemented method of analysing nuclear magnetic resonance, NMR, data of a target object is provided. The method comprises receiving NMR data of the target object, and analysing the received NMR data using a model of the diffusive behaviour of particles within the target object. The model includes a time parameter and a space parameter, the time parameter describing temporal characteristics of the diffusive behaviour of particles in the model and the space parameter describing spatial characteristics of (Continued)

the diffusive behaviour of particles in the model. The model is constrained such that the value of the time parameter and the value of the space parameter are related according to a correlation function. An apparatus for analysing nuclear magnetic resonance, NMR, data of a target object is also provided.

21 Claims, 15 Drawing Sheets

(56) References Cited

OTHER PUBLICATIONS

Alexander DC (2008). A general framework for experiment design in diffusion MRI and its application in measuring direct tissue-microstructure features. Magnetic Resonance in Medicine 60(2):439-448.
Alexander DC, Hubbard PL, Hall MG, Moore EA, Ptito M, Parker GJ, Dyrby TB (2010). Orientationally invariant indices of axon diameter and density from diffusion MRI. Neuroimage 52(4):1374-89.
Assaf Y, Basser PJ (2005). Composite hindered and restricted model of diffusion (Charmed) MR imaging of the human brain. Neuroimage 27(1):48-58.
Assaf Y, Blumenfeld-Katzir T, Yovel Y, Basser PJ (2008). AxCaliber: a method for measuring axon diameter distribution from diffusion MRI. Magnetic Resonance in Medicine 59(6):1347-54.
Benitez A, Jensen JH, Falangola MF, Nietert PJ, Helpern JA (2018). Modelling white matter tract integrity in aging with diffusional kurtosis imaging. Neurobiology of Aging 70:265-275.
Berberan-Santos MN (2005). Properties of the Mittag-Leffler Relaxation Function, Journal of Mathematical Chemistry, 38(4): 629-635.
Bonet-Carne E, Johnston E, Daducci A, Jacobs JG, Freeman A, Atkinson D, Hawkes DJ, Punwani S, Alexander DC, Panagiotaki E (2019). VERDICT-AMICO: Ultrafast fitting algorithm for non-invasive prostate microstructure characterization. NMR in Biomedicine 32(1):e4019.
Borlinhas F, Loução R, C Conceição R, Ferreira HA (2019). Gamma Distribution Model in the Evaluation of Breast Cancer Through Diffusion-Weighted MRI: A Preliminary Study. Journal of Magnetic Resonance Imaging. 50(1):230-238.
Falk Delgado A, Nilsson M, van Westen D, Falk Delgado A (2018). Glioma Grade Discrimination with MR Diffusion Kurtosis Imaging: A Meta-Analysis of Diagnostic Accuracy. Radiology, 287(1):119-127.
Farquharson S, Tournier JD, Calamante F, Fabinyi G, Schneider-Kolsky M, Jackson GD, Connelly A (2013). White matter fiber tractography: why we need to move beyond DTI. Journal of Neurosurgery 118(6):1367-77.
Gong NJ, Chan CC, Leung LM, Wong CS, Dibb R, Liu C (2017). Differential microstructural and morphological abnormalities in mild cognitive impairment and Alzheimer's disease: Evidence from cortical and deep gray matter. Human Brain Mapping, 38(5):2495-2508.
Hall MG and Barrick TR (2012). Two-step anomalous diffusion tensor imaging. NMR in Biomedicine. 25(2):286-94.
Ingo C, Barrick TR, Webb AG, Ronen I (2017), Accurate Pade global approximations for the Mittag-Leffler function, its inverse, and its partial derivatives to efficiently compute convergent power series. International Journal of Applied and Computational Mathematics 3 (2), 347-362.
Ingo C, Magin RL, Colon-Perez L, Triplett W, Mareci TH (2014). On random walks and entropy in diffusion-weighted magnetic resonance imaging studies of neural tissue. Magnetic Resonance Medicine, 71(2):617-27.
Ingo C, Sui Y, Chen Y, Parrish TB, Webb AG, Ronen U (2015). Parsimonious continuous time random walk models and kurtosis for diffusion in magnetic resonance of biological tissue. Frontiers In Physics 3, 11.
Jelescu IO, Veraart J, Adisetiyo V, Milla SS, Novikov DS, Fieremans E (2015). One diffusion acquisition and different white matter models: how does microstructure change in human early development based on WMTI and NODDI? Neuroimage 15;107:242-256.
Jelescu IO, Veraart J, Fieremans E, Novikov DS (2016). Degeneracy in model parameter estimation for multi-compartmental diffusion in neuronal tissue. NMR in Biomedicine 29(1):33- 47.
Jensen JH, Helpern JA. MRI quantification of non-Gaussian water diffusion by kurtosis analysis (2010). NMR in Biomedicine. 23(7):698-710.
Jensen JH, Helpern JA, Ramani A, Lu H, Kaczynski K (2005). Diffusional kurtosis imaging: the quantification of non-Gaussian water diffusion by means of magnetic resonance imaging. Magnetic Resonance in Medicine 53(6):1432-40.
Jeurissen B, Leemans A, Jones DK, Tournier JD, Sijbers J. (2011). Probabilistic fiber tracking using the residual bootstrap with constrained spherical deconvolution. Human Brain Mapping 32(3):461-79.
Jeurissen B, Tournier JD, Dhollander T, Connelly A, Sijbers J (2014). Multi-tissue constrained spherical deconvolution for improved analysis of multi-shell diffusion MRI data. Neuroimage 103:411-426.
Jurlewicz A, Kernb P, Meerschaert MM, Scheffler H-P (2012). Fractional governing equations for coupled random walks. Computers and Mathematics with Applications 64:3021-3036.
Lampinen B, Szczepankiewicz F, Mårtensson J, van Westen D, Sundgren PC, Nilsson M (2017). Neurite density imaging versus imaging of microscopic anisotropy in diffusion MRI: A model comparison using spherical tensor encoding. Neuroimage 147:517-531.
Luchko Y, (2019). Subordination principles for the multi-dimensional space-time-fractional diffusion-wave equation. Theory of Probability and Mathematical Statistics 98: 127-147.
Magin RL, Abdullah O, Baleanu D, Zhou XJ (2008). Anomalous diffusion expressed through fractional order differential operators in the Bloch-Torrey equation. Journal of Magnetic Resonance, 190(2):255-70.
Mainardi F, Luchko Y, Pagnini G (2001). The fundamental solution of the space-time fractional diffusion equation, Fractional Calculus and Applied Analysis, 4(2): 153-192.
Metzler R and Klafter J (2000) The Random Walk's Guide to Anomalous Diffusion: A Fractional Dynamics Approach. Physics Reports, 339, 1-77.
Novikov DS, Veraart J, Jelescu IO, Fieremans E (2018). Rotationally-invariant mapping of scalar and orientational metrics of neuronal microstructure with diffusion MRI. Neuroimage 174:518-538.
Oshio K, Shinmoto H, Mulkern RV (2014). Interpretation of diffusion MR imaging data using a gamma distribution model. Magnetic Resonance in Medicine 13(3):191-5.
Panagiotaki E, Chan RW, Dikaios N, Ahmed HU, O'Callaghan J, Freeman A, Atkinson D, Punwani S, Hawkes DJ, Alexander DC. Microstructural characterization of normal and malignant human prostate tissue with vascular, extracellular, and restricted diffusion for cytometry in tumours magnetic resonance imaging. Investigative Radiology 50(4):218-27.
Panagiotaki E, Walker-Samuel S, Siow B, Johnson SP, Rajkumar V, Pedley RB, Lythgoe MF, Alexander DC (2014). Noninvasive quantification of solid tumor microstructure using VERDICT MRI. Cancer Research 74(7):1902-12.
Praet J, Manyakov NV, Muchene L, Mai Z, Terzopoulos V, de Backer S, Torremans A, Guns PJ, Van De Casteele T, Bottelbergs A, Van Broeck B, Sijbers J, Smeets D, Shkedy Z, Bijnens L, Pemberton DJ, Schmidt ME, Van der Linden A, Verhoye M (2018). Diffusion kurtosis imaging allows the early detection and longitudinal follow-up of amyloid-?-induced pathology. Alzheimer's Research & Therapy, 10(1):1.
Raschke F, Barrick TR, Jones TL, Yang G, Ye X, Howe FA (2019). Tissue-type mapping of gliomas. Neuroimage Clin. 21:101648.
Tietze A, Hansen MB, Østergaard L, Jespersen SN, Sangill R, Lund TE, Geneser M, Hjelm M, Hansen B (2015). Mean Diffusional Kurtosis in Patients with Glioma: Initial Results with a Fast Imaging Method in a Clinical Setting. American Journal of Neuroradiology, 36(8):1472-8.

(56) References Cited

OTHER PUBLICATIONS

Veraart, J, Nunes D, Rudrapatna U, Fieremans E, Jones DK, Novikov DS, Noam Shemesh (2020). Noninvasive quantification of axon radii using diffusion MRI. eLife Journal, 9:e49855.

Wedeen VJ, Hagmann P, Tseng WY, Reese TG, Weisskoff RM (2005). Mapping complex tissue architecture with diffusion spectrum magnetic resonance imaging. Magnetic Resonance in Medicine 54(6):1377-86.

Yablonskiy DA, Bretthorst GL, Ackerman JJH (2003). Statistical Model for Diffusion Attenuated MR Signal, Magnetic Resonance in Medicine 50(4): 664-669.

Yin J, Sun H, Wang Z, Ni H, Shen W, Sun PZ (2018). Diffusion Kurtosis Imaging of Acute Infarction: Comparison with Routine Diffusion and Follow-up MR Imaging. Radiology 287(2):651-657.

Zhu LH, Zhang ZP, Wang FN, Cheng QH, Guo G (2019). Diffusion kurtosis imaging of microstructural changes in brain tissue affected by acute ischemic stroke in different locations. Neural Regeneration Research 14(2):272-279.

Nilsson et al., "Evaluating the accuracy and precision of a two-compartment Karger model using Monte Carlo simulations", Journal of Magnetic Resonance, vol. 206, No. 1, Sep. 1, 2010, pp. 59-67.

Fiermans et al., "Simulation and experimental verification of the diffusion in an anisotropic fiber phantom", Journal of Magnetic Resonance, vol. 190, No. 2, Nov. 1, 2007, pp. 189-199.

Yoram Cohan et al., "Highb-value q-space analysed diffusion-weighted MRS and MRI in neuronal tissues—a technical review", vol. 15, No. 7-8, Dec. 5, 2002, pp. 516-542.

\* cited by examiner

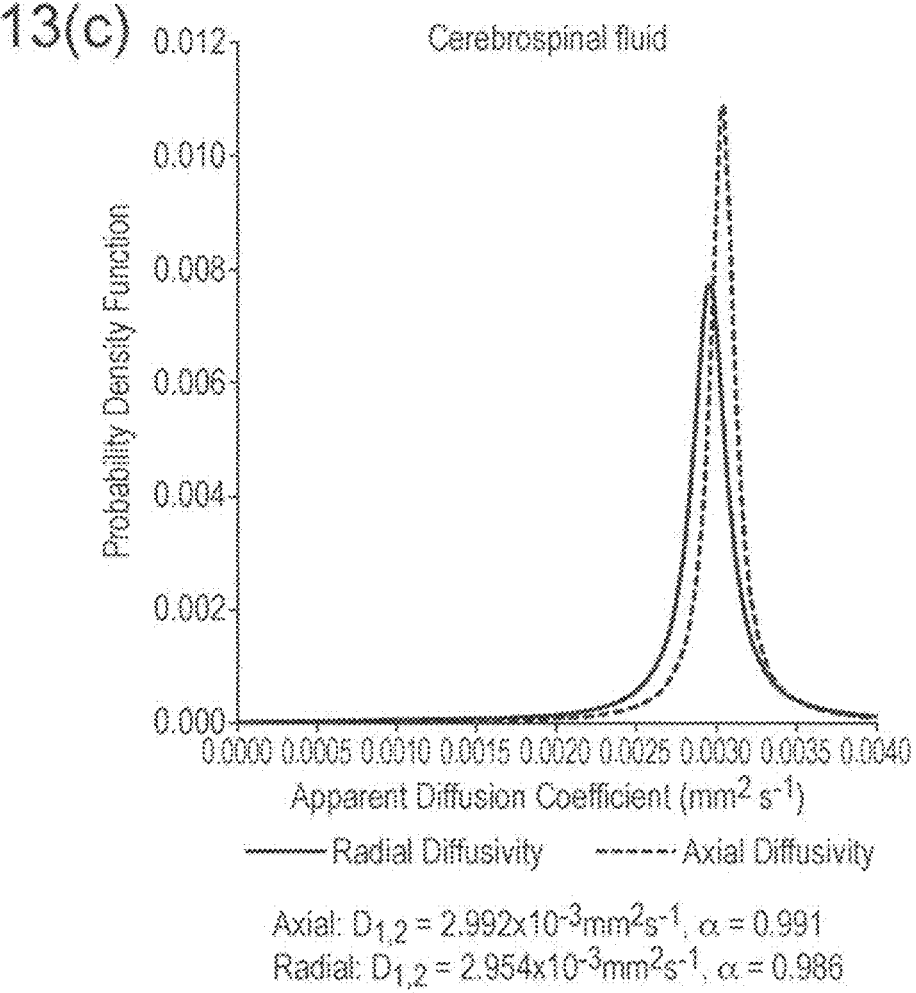
Fig. 13(c) Cerebrospinal fluid
Axial: $D_{1,2} = 2.992 \times 10^{-3}$ mm$^2$s$^{-1}$, $\alpha = 0.991$
Radial: $D_{1,2} = 2.954 \times 10^{-3}$ mm$^2$s$^{-1}$, $\alpha = 0.986$
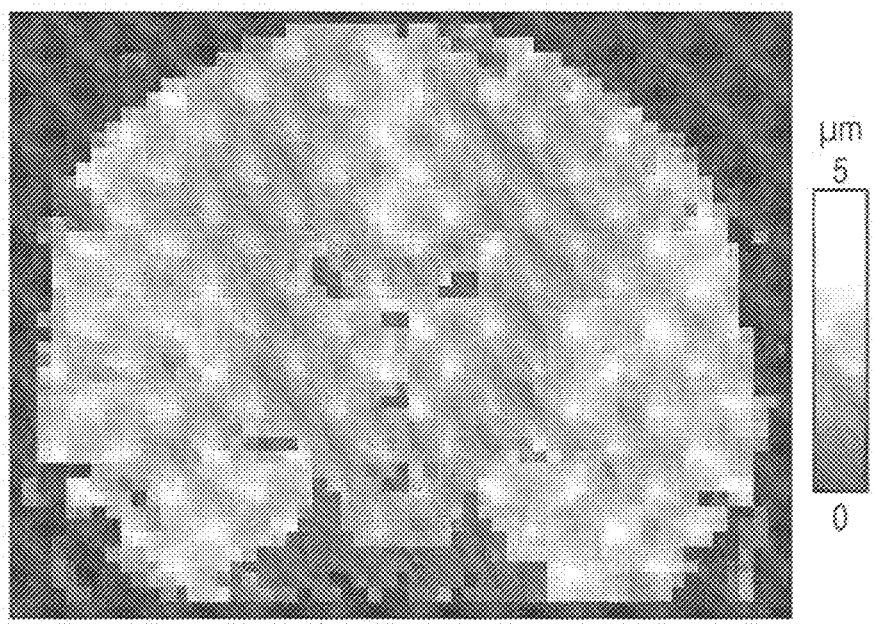
Fig. 14

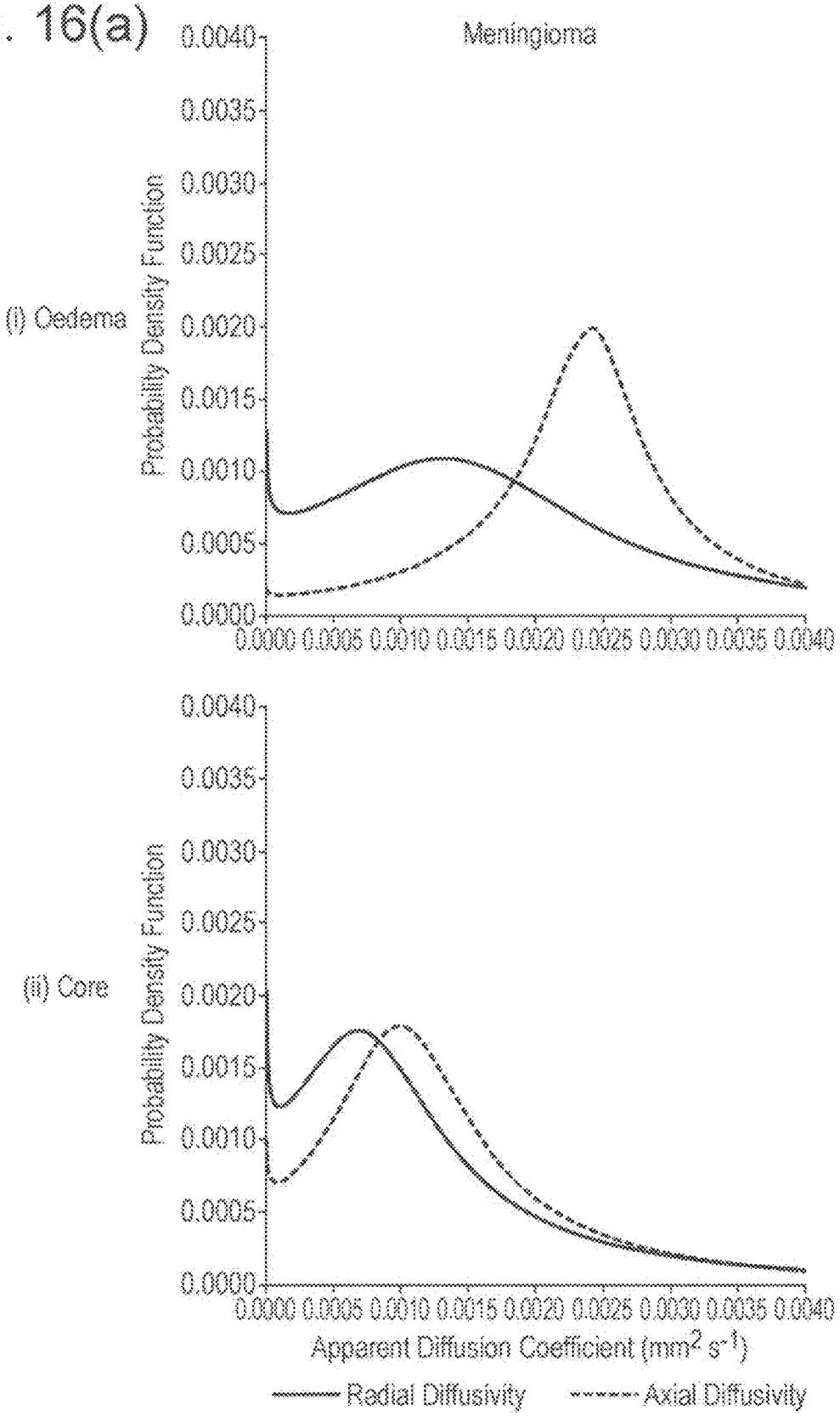

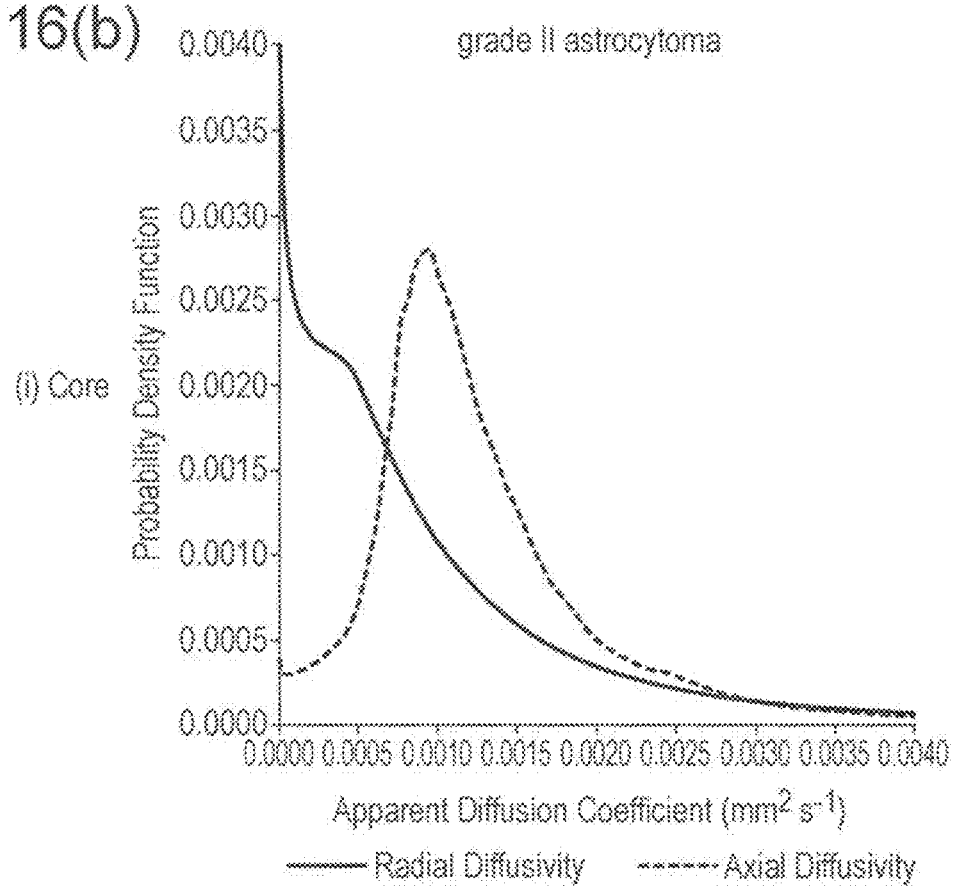

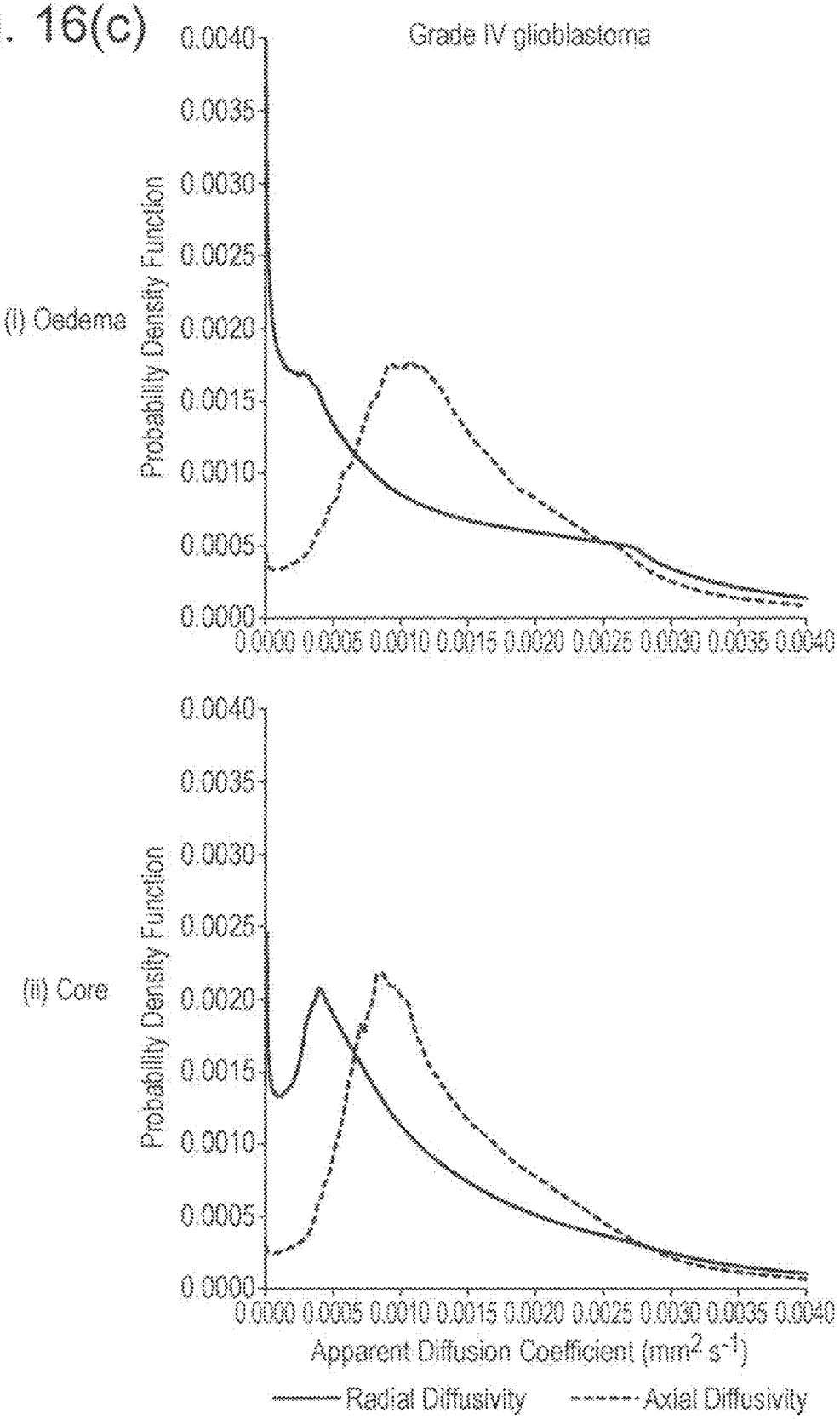

METHOD AND APPARATUS FOR QUASI-DIFFUSION MAGNETIC RESONANCE IMAGING

This application is a U.S. National Phase Application under 35 U.S.C. 371 of International Application No. PCT/GB2020/051639, filed on Jul. 8, 2020, which claims priority to British Patent Application No. 1909982.9, filed on Jul. 11, 2019. The entire disclosures of the above applications are expressly incorporated by reference herein.

The invention relates to computer-implemented methods for analysing data received from nuclear magnetic resonance measurements.

Nuclear magnetic resonance (NMR) is a well-known and powerful tool for analysing the properties and structure of materials. One particularly important application is magnetic resonance imaging (MRI), which is the leading method for clinical and research studies of the brain, and is widely used to image other biological systems as well. Development of well validated and robust quantitative imaging biomarkers is sought for increased diagnostic accuracy, decreased subjectivity and variability, automated analyses, and to provide robust endpoints for clinical trials [Abramson et al., 2015].

One application of NMR is in measuring the diffusion of particles, which can be used to infer details of the structure of the material in which they are diffusing. This can include measurements of, for example, shale rock formation in the oil and gas industry. In addition, one of many MRI neuroimaging methods is diffusion weighted imaging (DWI), which can quantify the mean diffusivity (MD, a measure reflecting the magnitude of microscopic random motion of water) in biological tissue. MD (a.k.a. the apparent diffusion coefficient, ADC in $mm^2s^{-1}$) changes with disease, damage or normal maturation and aging, due to the microscopic alterations in the structure of brain tissue. MD maps are routinely used to aid clinical diagnosis and prognosis, particularly for brain tumours and stroke. Brain tissue has a highly complex microstructure that is altered by lesions and degenerative diseases and DWI has become a major tool in the clinic and for research studies. For example, diffusion tensor imaging (DTI) detects directionality differences in diffusion (via a parameter called FA, the fractional anisotropy) and can track neuronal white matter connections between brain regions. FA is more sensitive at detecting degeneration of these tracts than MD, but is predominantly used in research due to the additional image acquisition time needed to acquire a diffusion tensor.

More recently Diffusional Kurtosis Imaging (DKI) [Jensen et al., 2005; Jensen & Helpern, 2010] has been introduced, which detects non-Gaussian diffusion (i.e. diffusion that is affected by interactions of water molecules with microstructural tissue components such as cell membranes), and provides greater sensitivity to subtle microstructural damage and early detection of pathological change. DKI is being widely investigated for its application to dementias [Gong et al., 2017, Praet et al., 2018] and brain tumours [Falk et al., 2018], by means of the diffusional kurtosis parameter (k). However, DKI uses a simple parameterisation of the diffusion signal that does not accurately represent actual physical diffusion processes within tissue and is instead a technique that provides a representation of the measured diffusion-weighted MRI signal as a function of the diffusion sensitisation parameter, the b-value [Jensen et al., 2005; Jensen & Helpern, 2010; Ingo et al., 2015]. Furthermore, due to limitations inherent in the simplistic parameterisation of Kurtosis, DKI cannot use the higher diffusion sensitisation capabilities of modern MRI systems as it cannot utilise diffusion sensitisations for which b>3000 s $mm^{-2}$ [Jensen & Helpern, 2010]. Consequently this technique does not provide stable parameterisation of diffusion MRI data, does not enable efficient or accurate computation of diffusion maps, and does not exploit the full capabilities of modern clinical MRI systems.

A second group of popular diffusion imaging techniques are those predicated on strong geometrical assumptions of the shape and number of tissue microstructural compartments in neural tissue, which range from highly anisotropic tubular structures that represent axons, diffusion tensors that represent extracellular spaces and hollow spheres that represent isotropic compartments and free water [CHARMED Assaf & Basser, 2005; AxCaliber Assaf et al., 2008; ActiveAx Alexander et al., 2008, 2010; NODDI Zhang et al., 2012; VERDICT Panagiotaki et al., 2014; 2015]. Although these types of techniques have been shown to provide potentially useful clinical information these models are challenging to fit and exhibit acquisition and parameter based bias [Jelescu et al., 2015] that limit their application in clinical practice. In addition, the most widely used of these models, NODDI, has constraints and assumptions that appear to be invalid [Lampinen et al., 2017] and limitations due to model degeneracy [Jelescu et al., 2016] that cannot be adequately resolved [Novikov et al., 2018]. Furthermore, these techniques are not readily applicable to organs outside the central nervous system without adaption of geometrical assumptions and algorithmic recalibration [Bonet-Carne et al., 2019].

MRI diffusion parameters can only be correctly and accurately computed, as well as assigned a strictly meaningful physical interpretation, if a correct mathematical model of the diffusion process is applied to the set of diffusion weighted MR images that are acquired. An appropriate mathematical model allows accurate computation of MRI diffusion parameters that may be physically interpreted. In current practice, the measurement of different aspects of tissue water diffusion in the diffusion environment is achieved using a variety of mathematical models, approximations and optimised data acquisitions. This lack of generalisability is a limitation of these diffusion techniques. In addition, the computed images that represent diffusion parameters produced using these techniques are very susceptible to noise, leading to the requirement for long acquisition times that enable diffusion measurements to be estimated with low enough variance to be useful. In some cases, it may also be desirable for these techniques to provide data that can be used to identify white matter fibre orientations within a voxel [Jeurissen et al., 2014] for white matter tractography [Jeurissen et al., 2011; Farquharson et al., 2013] and this may further extend acquisition times due to the need for greater angular resolution of diffusion gradient directions.

For new MRI techniques to be clinically useful there is a need for rapid image acquisition to ensure patient comfort, maximise image quality (by minimising time for patient movement) and to minimise the economic cost. This means there is a requirement to obtain images with excellent signal to noise and tissue contrast to noise ratios at short acquisition times. Current clinical acquisitions are 30 seconds for conventional DWI and 1 minute for clinical DTI and 5 minutes for conventional DTI. Current DKI techniques can be acquired for up to 22 minutes in research studies [e.g. Benitez et al., 2018] but have also been acquired in approximately 2 minutes in clinical studies [e.g. Tietze et al., 2015; Yin et al., 2018]. Although several fast, potentially clinically applicable acquisition techniques are available for DKI [Tietze et al., 2015; Yin et al., 2018] these are not tensor acquisitions that can derive the anisotropy of diffusion within brain tissue structures, and they have low signal to noise and contrast to noise ratios.

It is an object of the invention to provide an improved quantitative NMR data analysis method which allows faster data acquisition with lower noise and higher accuracy in a low signal to noise environment. Such an invention would have particular advantages in aiding clinical staff in quickly and accurately detecting microstructural damage in disease, and would have clear applications in stroke, brain tumours and dementia. Preferably, this method would also provide data that can be used to identify tissue fibre orientations, for example white matter fibre orientations for white matter tractography.

According to a first aspect of the invention, there is provided a computer-implemented method of analysing nuclear magnetic resonance, NMR, data of a target object, wherein the method comprises receiving NMR data of the target object, analysing the received NMR data using a model of the diffusive behaviour of particles within the target object, wherein the model includes a time parameter and a space parameter, the time parameter describing temporal characteristics of the diffusive behaviour of particles in the model and the space parameter describing spatial characteristics of the diffusive behaviour of particles in the model, and the model is constrained such that the value of the time parameter and the value of the space parameter are related according to a correlation function.

This correlation function is a mathematical constraint on the relationship between the time and space parameters. By constraining the model of the diffusive behaviour of particles, the number of degrees of freedom in the model is reduced. This reduces the amount of data that is required to analyse the data using the model to achieve a satisfactory fit of the data to the model, which reduces the necessary acquisition times. The inventors have found that constraining the values of the time and space parameter to be related according to a correlation function provides a particularly effective way to constrain the model to achieve these advantages.

In an embodiment, the target object is a human or animal subject, and the NMR data comprises magnetic resonance imaging, MRI, data. Using NMR techniques to perform imaging of human or animal subjects is a high demand application in medical and veterinary fields.

In an embodiment, the model comprises a random walk model. By using a model of the actual physical diffusion processes that affect the signal in NMR methodology, the computed values that represent diffusion parameters are less susceptible to noise, reducing the acquisition times needed to enable diffusion measurements to be estimated with low enough variance to be useful.

In an embodiment, the space parameter describes a size of steps made by the particles in the random walk model. Using the space parameter to describe the step size ties the model more closely to the microscopic behaviour of the particles, and allows it to more directly model their behaviour.

In an embodiment, the space parameter is an exponent relating to a probability density function of steps made by the particles in the random walk model. Particles do not make steps of uniform sizes at all times, and so using a probability density function to describe the size of steps made provides a more accurate description of particle behaviour.

In an embodiment, the time parameter describes a time between steps made by the particles in the random walk model. Using the time parameter to describe the time between steps ties the model more closely to the microscopic behaviour of the particles, and allows it to more directly model their behaviour.

In an embodiment, the time parameter describes an exponent relating to a probability density function of time between steps made by the particles in the random walk model. Particles do not make steps at regular time intervals, and so using a probability density function to describe the time between steps provides a more accurate description of particle behaviour.

In an embodiment, the model comprises a continuous-time random walk model. By using a continuous time random walk model, the diffusive behaviour of particles can be very generally modelled, so that it more accurately reflects the actual behaviour of particles.

In an embodiment, the correlation function is such that the pairs of values of the time parameter and the space parameter satisfying the correlation function comprise a pair of values where the diffusive behaviour of the particles in the model obeys a Gaussian random walk. Constraining the model according to a correlation function is most effective when the correlation function is such as to cause the diffusive behaviour of particles in the model to behave in a manner more similar to Gaussian diffusion.

In an embodiment, the correlation function is such that the values of the time parameter and the space parameter satisfying the correlation function further satisfy $|\beta - 2\alpha| < 0.5$ and $0 \leq \alpha \leq 1$ and $0 \leq \beta \leq 2$. The constraint is more effective when possible values of the time and space parameter are such as to more closely follow a Gaussian-like behaviour, which is neither sub-diffusive nor super-diffusive. Therefore, embodiments where the time and space parameters are constrained by the correlation function to follow Gaussian-like behaviour more closely can provide improved performance.

In an embodiment, the correlation function is such that the time parameter increases monotonically as a function of the space parameter. A monotonically increasing correlation function means that there is a one-to-one correspondence between allowed values of the time and space parameters, which can simplify analysis using the correlation function.

In an embodiment, the correlation function is such that the time parameter is directly proportional to the space parameter. When the time parameter is directly proportional to the space parameter, the model can be greatly simplified, as one of the two parameters can be replaced by a simple multiple of the other. This leads to computational advantages, allowing faster data acquisition and processing.

In an embodiment, the correlation function is such that the diffusive behaviour of particles in the model is quasi-diffusive. The particular choice of quasi-diffusive behaviour has been found to give improved accuracy while maintaining the advantages of faster processing provided by direct proportionality between the time and space parameters.

In an embodiment, the step of analysing the NMR data comprises calculating a three-dimensional representation of a structure within the target object on the basis of the model, the calculation using a variation in directionality of the diffusive behaviour of particles within the target object as a function of position within the target object, and producing output data based on the three-dimensional representation. An important application of NMR imaging is to determine the structure of target objects, and using the directionality of diffusive behaviour can provide information about the constraints on movement of particles determined by the structure of the target object.

In an embodiment, the step of producing output data comprises applying a tractography algorithm to determine the orientations of elements of the structure within the target object. Directionality data on diffusive behaviour can provide valuable information about the structure of materials such as tissue fibres in the human or animal body, and in particular brain tissue fibres such as white matter fibres via tractography.

In an embodiment, the method further comprises determining, on the basis of the output data, information about a microstructure within the target object. Once a three-dimensional representation of a target object is obtained, more information can be determined about microscopic structure within the target object. This could include orientation or size of filaments or fibres within a particular region of the object, for example.

In an embodiment, the method further comprises identifying, on the basis of the information about the microstructure, a structure type of a target region containing the microstructure. Structural information can be used to classify or identify parts of a target object. This is valuable for determining what structures are present, and whether the structures display any abnormalities from what would be expected of that structure in similar, previously analysed target objects.

In an embodiment, the target object is a human or animal subject, and the identified structure type is associated with a set of one or more pathologies. By comparing the microstructures identified in the target object with known microstructures and known properties of those microstructures, it can be determined whether the target object displays any abnormalities that correspond to particular pathologies.

In an embodiment, the step of analysing the NMR data comprises calculating a diffusion spectrum for one or more regions of the target object, the diffusion spectrum of a region being a probability density function for values of a diffusion parameter characterising the diffusive behaviour of particles within the region. Calculating a diffusion spectrum provides an output which is closely linked to the physical diffusion dynamics within the target object, and thereby more directly represents the physical properties of the target object.

In an embodiment the diffusion parameter is one of an apparent diffusion coefficient and a length scale of a structure of the target object within the region. These parameters are closely linked to the physical properties of the target object and are readily interpretable.

In an embodiment calculating the diffusion spectrum comprises taking an integral transform of the model of the diffusive behaviour of particles within the target object, wherein optionally the integral transform is a Laplace transform or a Fourier transform. Integral transforms are a computationally well-understood and efficient way to perform variable transformations that are particularly suitable to the present method due to the typical form of the model used.

According to a second aspect of the invention, there is provided an apparatus for analysing nuclear magnetic resonance, NMR, data of a target object, wherein the apparatus comprises receiving means configured to receive NMR data of the target object, and analysis means configured to analyse the NMR data using a model of the diffusive behaviour of particles within the target object, wherein the model includes a time parameter and a space parameter, the time parameter describing temporal characteristics of the diffusive behaviour of particles in the model and the space parameter describing spatial characteristics of the diffusive behaviour of particles in the model, and the model is constrained such that the value of the time parameter and the value of the space parameter are related according to a correlation function.

Thereby, there is provided an apparatus configured to analyse NMR data using a constraint on a model of the diffusive behaviour of particles that reduces the number of degrees of freedom in the model. This reduces the amount of data that is required to analyse the data using the model to achieve a satisfactory fit of the data to the model, which reduces the necessary acquisition times. The inventors have found that constraining the values of the time and space parameter to be related according to a correlation function provides a particularly effective way to constrain the model to achieve these advantages.

Embodiments of the invention will now be described, by way of example only, with reference to the accompanying drawings in which corresponding reference symbols represent corresponding parts, and in which:

FIG. 14 shows the effective pore radius image computed using QDI within the brain of a healthy subject;

FIG. 16 shows diffusion spectra of a dMRI decay curve in QDI calculated for brain tumour regions within a human subject, for different types of tumour.

A computer-implemented method of analysing nuclear magnetic resonance (NMR) data of a target object is provided. In an embodiment, the target object is a human or animal subject, and the NMR data comprises magnetic resonance imaging (MRI) data. However, the method is applicable to analysing data from other target objects, for example rock formations such as oil shale or other porous media. When used for MRI data, the method may be applied to imaging of any part of the human or animal body, but is particularly advantageous when applied to imaging a brain. The method is particularly suited to detecting changes in brain tissue associated with stroke, brain tumours and dementia. The method is applicable to clinical diagnosis and prognosis, as well as research studies.

Figure 10:
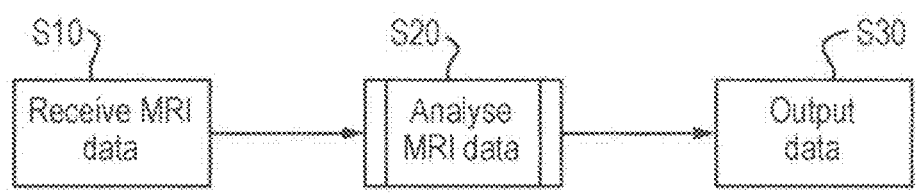
FIG. 10 is a flowchart of the method according to an embodiment.

As shown in the flowchart of FIG. 10, the method comprises a step S10 of receiving NMR data of the target object, for example a human or animal subject, and a step S20 of analysing the received NMR data using a model of the diffusive behaviour of particles within the target object. In an embodiment, the NMR data comprises NMR diffusion signal attenuation, and the method comprises receiving such data. In an embodiment the particles comprise molecules commonly present in human or animal subjects, for example water molecules.

The MRI data may be acquired using any standard MRI system, such as are commonly used in clinical and research settings. An example of such a system is a 3T Philips Achieva Dual TX MR scanner.

The model of the diffusive behaviour of particles includes a time parameter and a space parameter, the time parameter describing temporal characteristics of the diffusive behaviour of particles in the model and the space parameter describing spatial characteristics of the diffusive behaviour of particles in the model. The model is constrained such that the value of the time parameter and the value of the space parameter are related according to a correlation function.

In an embodiment, the model comprises a random walk model. In such an embodiment, the space parameter may describe a size of steps made by the particles in the random walk model, for example, the space parameter may be an exponent relating to a probability density function of steps made by the particles in the random walk model. The time parameter may describe a time between steps made by the particles in the random walk model, for example the time parameter may be an exponent relating to a probability density function of time between steps made by the particles in the random walk model. In an embodiment the model comprises a continuous-time random walk model.

The analysis method provided herein is referred to as quasi-diffusion NMR (QD-NMR) which can be applied for MRI as quasi-diffusion magnetic resonance imaging (QDI). In a preferred embodiment, QDI is based on the continuous time random walk (CTRW) as previously formulated for stochastic diffusion properties [Metzler and Klafter, 2000; Klages et al., 2008, Jurlewicz et al., 2012], which is a general diffusion model that can be applied to any multi-compartment structure within which there is molecular diffusion, and describes non-Gaussian diffusion.

This method may be applied to MRI diffusion-weighted signal within an image voxel. The QDI method also provides accurate and stable fitting of diffusion MRI data and overcomes the limitations of DKI. This enables derivation of standard mean diffusivity and diffusion tensor images as well as maps analogous to k [Jensen et al., 2005; Jensen & Helpern, 2010] and their anisotropic characteristics in a single optimised acquisition. These novel QDI maps are acquired using an extremely fast MR imaging protocol with both high contrast-to-noise and high signal-to-noise ratios which may be implemented on a standard clinical MRI system for routine clinical work. Furthermore, QDI does not involve strong geometrical assumptions pertaining to the tissue microstructure and can be applied to organs outside the central nervous system. QDI data can also be used to perform diffusion tractography to delineate the connectivity of white matter fibres throughout the brain.

The embodiment of QDI described in detail herein is a development of the CTRW model [Metzler & Klafter, 2000; Klages et al., 2008] previously applied to MRI [Magin et al., 2008; Ingo et al., 2014] and rodent brain [Ingo et al., 2014]. The CTRW model defines exponents $\alpha$ and $\beta$ that relate to how long a water molecule waits in one place (i.e. waiting time), and how far it then jumps (i.e. step length), respectively. This model also provides a diffusion coefficient $D_{\alpha,\beta}$ (in $mm^\beta s^{-\alpha}$) analogous to the conventional ADC, but not equivalent except in the case of the Gaussian limit such as the diffusion found in CSF or cysts[1]. MRI diffusion signal attenuation is represented by the CTRW model as, $$p(q, \bar{\Delta}) = S_0 \sum_{k=0}^{\infty} \frac{(-D_{\alpha,\beta} q^\beta \bar{\Delta}^\alpha)^k}{\Gamma(\alpha k + 1)}, \quad [Eq. 1]$$

for $0 < \alpha \leq 1$ (the time exponent) and $1 \leq \beta \leq 2$ (the space exponent), where $S_0$ represents the signal without diffusion sensitisation (with $S_0 = 1$ if Eq. 1 is normalised) and q (a parameterisation of q-space) and $\bar{\Delta}$ (the diffusion time in secs) are acquisition parameters that define the diffusion sensitisation $$\left(b = (\gamma g \delta)^2 \left(\Delta - \frac{\delta}{3}\right) = q^2 \bar{\Delta}\right)$$

[Ingo et al. 2014], where g is diffusion gradient strength in $mTm^{-1}$.

[1] Magin et al., (2008) and Ingo et al., (2014) have shown that the units of D may be recovered (i.e. for $D_{1,2}$ in $mm^2s^{-1}$) but this requires inclusion of further model parameters which require longer data acquisition and can cause instability in model parameter estimation and data fitting.

Figure 1A:
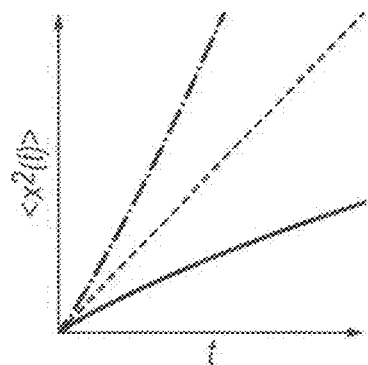
FIG. 1 shows graphs of stochastic properties of diffusion processes.
Figure 1B:
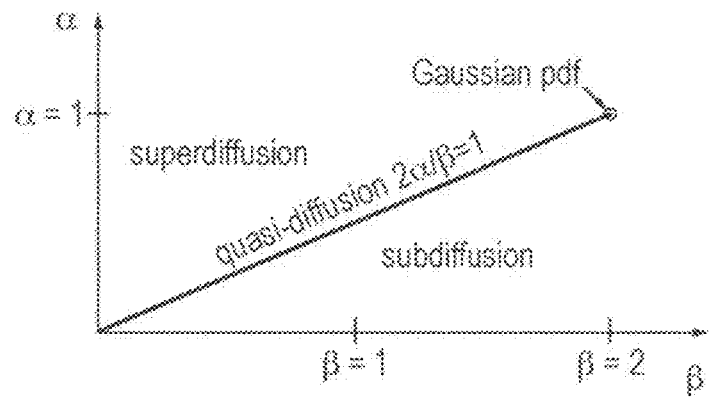

In the general version of the CTRW model [Eq. 1] the scaling behaviour of time and space is decoupled and provides potentially uncorrelated $\alpha$ and $\beta$ exponents. This is illustrated in FIG. 1, which shows stochastic properties of diffusion processes that may be determined using the general CTRW model. Graph (a) shows mean squared displacement with respect to diffusion time for sub-diffusion (black line), super-diffusion (grey line) and regular Gaussian diffusion (dotted line). Graph (b) shows the diffusion phase diagram and indicates the type of diffusion processes as identified by the time, a, and space, $\beta$, fractional exponents (adapted from Metzler & Klafter, 2000; Klages et al., 2008; Ingo et al., 2014). Regular Gaussian diffusion occurs when $\alpha=1$ and $\beta=2$, with superdiffusion when $2\alpha/\beta > 1$ and subdiffusion when $2\alpha/\beta < 1$. Quasi-diffusion occurs when $2\alpha/\beta = 1$ (i.e. $2\alpha = \beta$).

Figure 2:
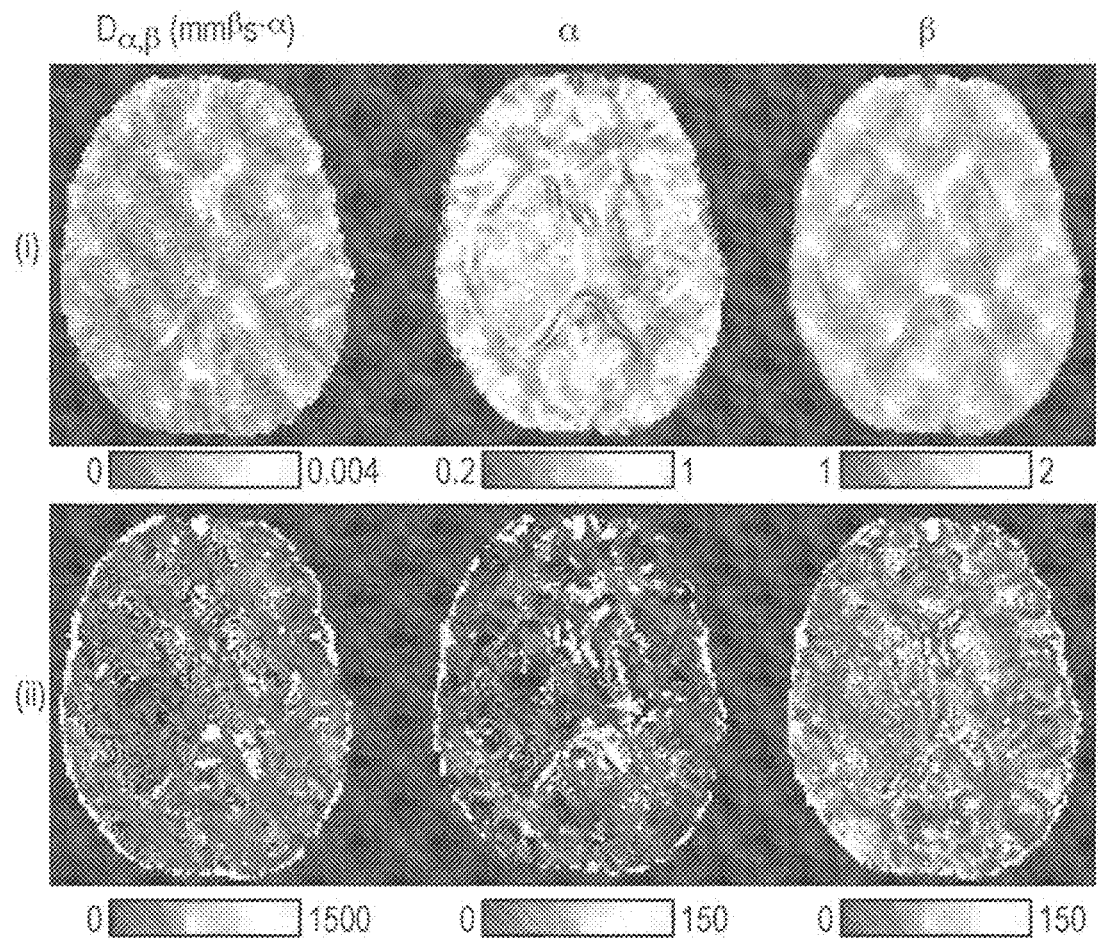
FIG. 2 shows diffusion parameter maps computed using the CTRW model.

However, the general CTRW model requires NMR data acquisition across multiple q and $\bar{\Delta}$ values and for DWI is not currently clinically feasible due to long acquisition times and limitations of the scanner electronics and hardware. If DWI is acquired in a pragmatic, clinically feasible manner by keeping $\bar{\Delta}$ constant and by altering q (i.e. by changing diffusion gradient strength, g) it is possible to compute $D_{\alpha,\beta}$, $\alpha$ and $\beta$ maps using the general CTRW model. However, under such a constraint the data fitting is unstable. This is illustrated in FIG. 2, which shows maps computed using the general CTRW model [Eq. 1] when DWI is acquired with constant $\bar{\Delta}$. Row (i) shows maps of $D_{\alpha,\beta}$, $\alpha$ and $\beta$, demonstrating that the estimated maps are noisy. Row (ii) shows percentage error maps for, from left to right, $D_{\alpha,\beta}$, $\alpha$ and $\beta$, demonstrating that the estimated errors are large. An additional problem with this technique is that it is extremely difficult to recover standard units for the diffusion coefficient (i.e. from mm$^\beta$s$^{-\alpha}$ to mm$^2$s$^{-1}$).

To solve these problems, the embodiment of the method described herein allows simplification of the general CTRW model by a coupling of the α and β exponents to allow data acquisition in clinically feasible time that also provides stable model for parameter estimates. In other words, the model of the diffusive behaviour is constrained such that the time parameter α and the space parameter β are related according to a correlation function. The correlation function defines exactly how the time and space parameters are coupled, and can be represented by a line in the diffusion phase diagram shown in FIG. 1(b).

Specifically, in the general CTRW diffusion model the mean squared displacement of spins is given by $$\langle x^2 \rangle \sim t^{\frac{2\alpha}{\beta}}$$

and Gaussian diffusion by α=1 and β=2, such that $\langle x^2 \rangle \sim t$. In an embodiment, the correlation function is such that the pairs of values of the time parameter and the space parameter satisfying the correlation function comprise a pair of values where the diffusive behaviour of the particles in the model obeys a Gaussian random walk, and so constitutes Gaussian diffusion. The Gaussian random walk describes a system where the size of steps obeys a normal (Gaussian) distribution. Therefore, in this embodiment, the correlation function passes through the α=1 and β=2 point in the diffusion phase diagram.

The method is more effective when the diffusive behaviour of the particles more closely resembles quasi-diffusive behaviour. Thus, the constraint is most effective when the values of the correlation function are close to the quasi-diffusion line in the diffusion phase diagram.

In an embodiment, the correlation function is such that the time parameter increases monotonically as a function of the space parameter. For example, the correlation function may be such that the time parameter is linearly related to the space parameter for at least a range of values of the time parameter, wherein optionally the range covers at least 50% of the set of values of the time parameter used in the model, optionally 75%, optionally 100%. Further, the correlation function may be such that the time parameter is directly proportional to the space parameter.

In an embodiment, the correlation function is such that the values of the time parameter and the space parameter satisfying the correlation function further satisfy 0≤α≤1 and 0≤β≤2, optionally 1≤β≤2.

In an embodiment, the correlation function is such that the values of the time parameter and the space parameter satisfying the correlation function further satisfy |β−2α|<0.5, preferably |β−2α|<0.3, more preferably |β−2α|<0.1, more preferably |β−2α|<0.05. In these embodiments, the values of the time and space parameter are constrained to lie more closely to the quasi-diffusion line in the diffusion phase diagram, which improves the accuracy and reduces the noise of data output from the method.

If the same heuristic scaling relation of position with time continues to hold for non-Gaussian diffusion as for Gaussian diffusion, then $\langle x \rangle \sim t$ and 2α/β=1 in the CTRW model. In this case the general CTRW diffusion model is constrained to become a model of Gaussian-like diffusion and represents neither a superdiffusive or subdiffusive process. Instead this type of diffusion represents a quasi-diffusion process [Dynkin, 1965]. Since an important characteristic of the constraint introduced by this embodiment is to model the diffusive behaviour such that it has a similar heuristic scaling to Gaussian diffusion, it is advantageous to ensure that the correlation function includes the Gaussian diffusion point in the α and β phase diagram. In an embodiment, the correlation function is such that the diffusive behaviour of particles in the model is quasi-diffusive. It has been found that this quasi-diffusive model provides high signal to noise and contrast to noise images leading to very good results when applied to the analysis of MRI data of the brain.

Figure 3:
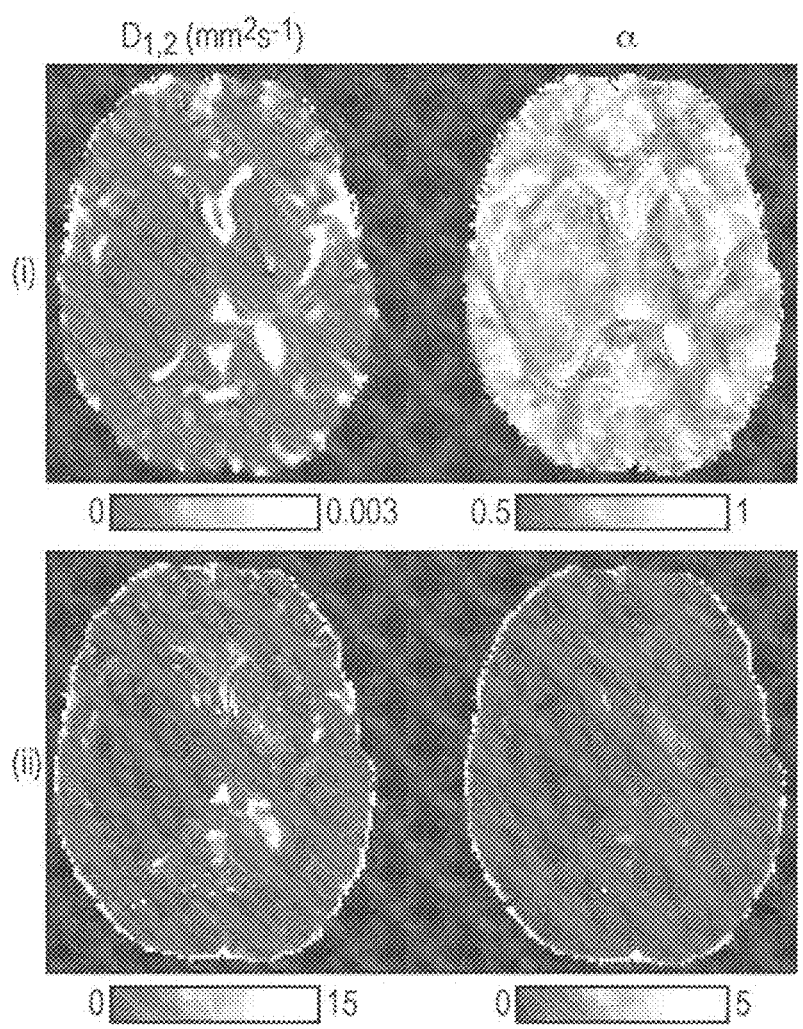
FIG. 3 shows diffusion parameter maps computed by applying the quasi-diffusion model.

By substitution of 2α=β in Eq. 1 we obtain a particularly advantageous embodiment, the quasi-diffusion model, $$p(q, \bar{\Delta}) = S_0 \sum_{k=0}^{\infty} \frac{(-D_{\alpha,2\alpha} q^{2\alpha} \bar{\Delta}^\alpha)^k}{\Gamma(\alpha k + 1)} = S_0 \sum_{k=0}^{\infty} \frac{(-(D_{1,2} b)^\alpha)^k}{\Gamma(\alpha k + 1)} = p(b), \quad [\text{Eq. 2}]$$

where $D_{\alpha,2,\alpha} = D_{1,2}{}^\alpha$, which parameterises the MRI diffusion signal attenuation by b-value and provides a diffusion coefficient $D_{1,2}$ in mm$^2$s$^{-1}$, which is the conventional ADC. In Eq. 2 the α stretching exponent represents a range of diffusion properties from Gaussian diffusion (α=1) through non-Gaussian diffusion (0<α<1). Essentially, QDI parameterises the signal decay according to rate (i.e. D) and shape (i.e. a). In an embodiment, QDI maps are rapidly computed by using Padé approximation of power series [Ingo et al., 2017] and model fitting using the Levenberg-Marquadt algorithm [Ingo et al., 2017]. FIG. 3 illustrates the improvement in data fitting and measurement estimation offered by the quasi-diffusion technique when compared to the same data shown in FIG. 2 for the general CTRW model. Specifically, FIG. 3 shows maps computed by applying the quasi-diffusion model [Eq. 2] to the same data as shown in FIG. 2. Row (i) shows maps of $D_{1,2}$ and α. Row (ii) shows percentage error maps for, from left to right, $D_{1,2}$ and α. Compared to FIG. 2 the quasi-diffusion model provides a quantifiable increase in signal to noise ratio, contrast to noise ratio and reduction in percentage error for computed measures.

QDI has several theoretical advantages over DKI and other similar techniques that improve inference of calculated measures and improve stability of model parameter estimates. These advantages are as follows: (a) the QDI model is related to physical processes of diffusion since it is based on a model of the diffusive behaviour of particles, in particular the CTRW model in some embodiments; (b) the QDI model enables diffusion sensitisation to be increased to the maximum capability of current and future MRI systems, whereas for DKI the theoretical maximum b-value is limited (i.e. to b≤3000 s mm$^{-2}$ [Jensen et al., 2005; Ingo et al., 2015]); (c) QDI involves computation of an infinite power series (see Eq. 2) based on diffusion signal attenuation using the Mittag-Leffler function, which is in contrast to DKI that uses a truncated (quadratic) power series approximation that is not modelled on physical behaviour of diffusion processes and produces fitting errors [Ingo et al., 2015].

Figure 4:
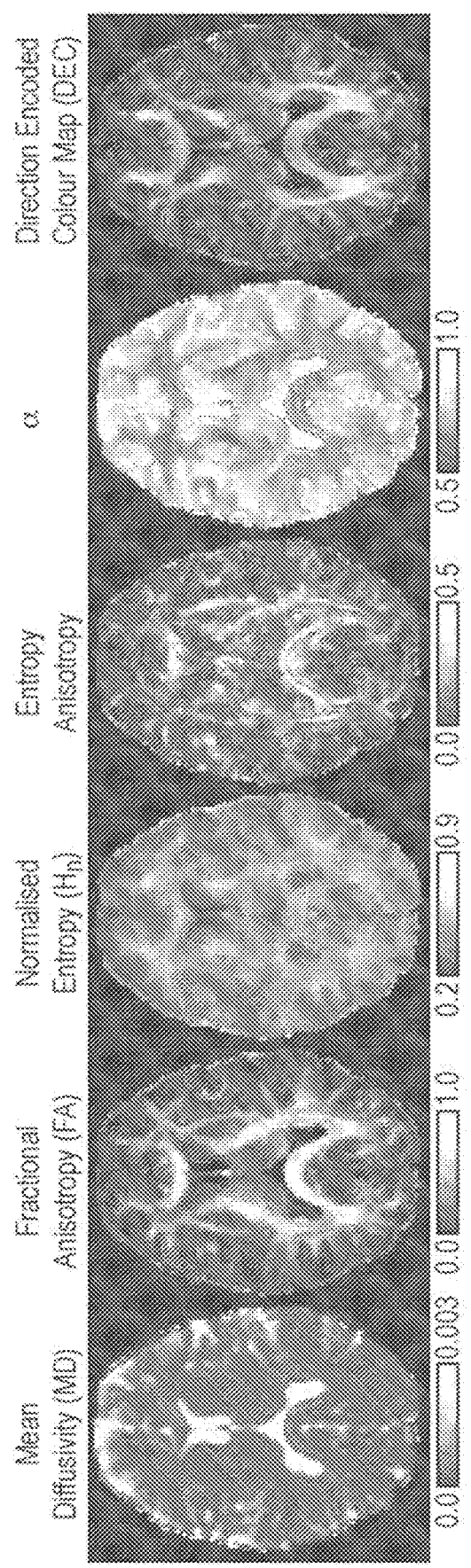
FIG. 4 shows quasi-diffusion tensor imaging data acquired on a control subject.
Figure 5:
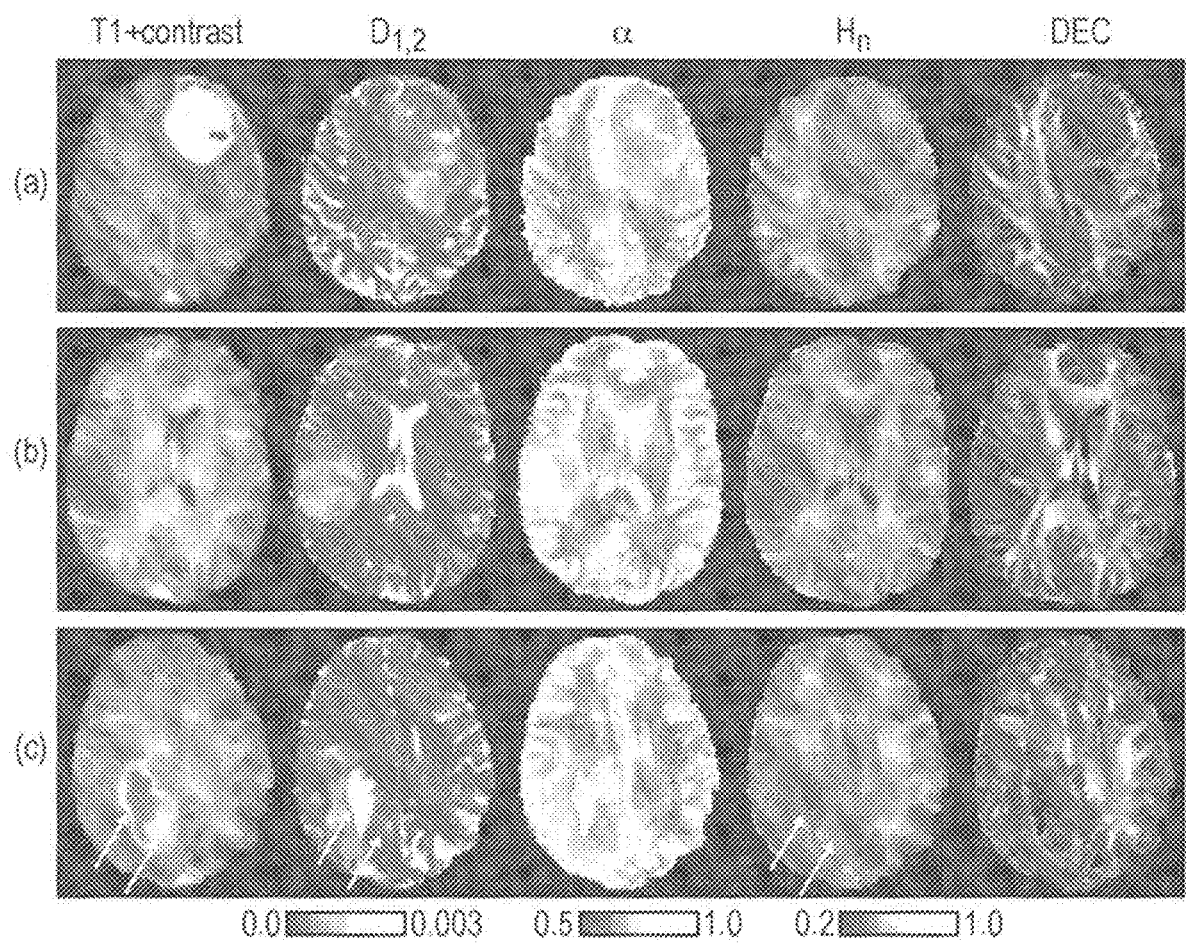
FIG. 5 shows quasi-diffusion tensor imaging maps of brain tumour cases.
Figure 6:
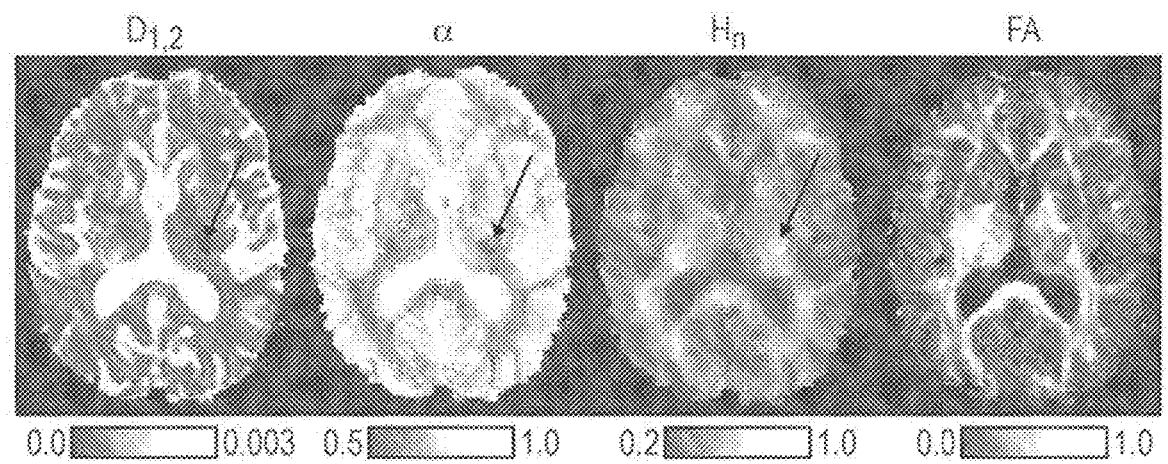
FIG. 6 shows quasi-diffusion tensor imaging maps of an acute stroke case.

The QDI technique does not directly produce an estimation of diffusional kurtosis from the model fitting [Eq. 2] but instead allows computation of a measurement that is analogous to diffusional kurtosis. Therefore, in an embodiment, the method may involve calculating output data from the MRI data on the basis of the model. The output data can include the normalised entropy ($H_n$) of the diffusion signal attenuation [Ingo et al., 2014]. $H_n$ represents the complexity of the diffusion signal within which the water is diffusing [Ingo et al., 2014; Ingo et al., 2015], and is computed from the decay curve obtained by fitting Eq. 2 to data by, $$H_n(X) = \frac{1}{\log(N)} \int_{i=1}^{N} p(x_i) \log(p(x_i)), \quad [\text{Eq. 3}]$$

which in the notation of [Eq. 2] and for $S_0=1$ can be written as, $$H_n(p(q, \bar{\Delta})) = -\frac{1}{\log(N)} \sum_{i=1}^{N} p(q_i, \bar{\Delta}) \log(p(q_i, \bar{\Delta})), \quad [\text{Eq. 4}]$$

where $0<H_n<1$, and N is the number of measurements made from the fitted decay curve. Normalised entropy has similar image contrast to kurtosis maps computed from DKI, as is shown in our preliminary analysis. This is demonstrated using data shown later. Furthermore, as shown in FIGS. 4 to 6, QDI produces images with higher contrast and signal to noise than DKI from a short MRI data acquisition.

Further parameters may also be calculated on the basis of the model. Therefore, the output data may include one or more of: a mean diffusivity, a fractional anisotropy, an apparent diffusion coefficient, a normalised entropy, an entropy anisotropy, the space parameter, or the time parameter.

Figure 11:
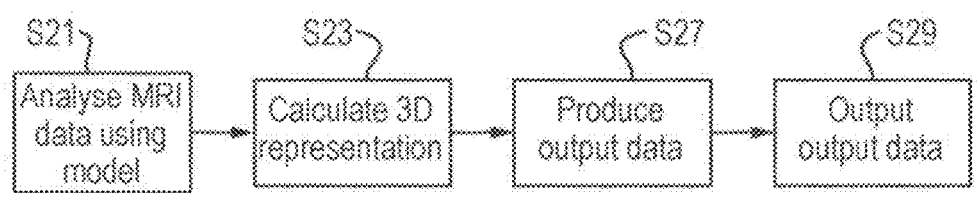
FIG. 11 is a flowchart for the analysis step of the method according to an embodiment.

Analysis of the NMR and/or MRI data using the model can also provide information about the structure of the target object. In an embodiment illustrated in the flowchart of FIG. 11, the step S20 of analysing the NMR data comprises a step S23 of calculating a three-dimensional representation of a structure of the target object on the basis of the model, the calculation using a variation in directionality of the diffusive behaviour of particles within the target object as a function of position within the target object; and a step S27 of producing output data based on the three-dimensional representation.

Observation of diffusive behaviour in different directions can provide information about microstructures within the target object. For example, microstructures comprising long, thin fibres will display higher diffusivity along the fibre axis than in the other perpendicular directions. These differences can be analysed to determine orientation and structure of features within the target object. In an embodiment, the step S27 of producing output data comprises applying a tractography algorithm to determine the orientations of elements of the structure of the target object. Although typically used to detect tissue fibre orientations in the human brain, tractography algorithms are also applicable to determining other types of structure, such as cracks or pores in geological layers.

In an embodiment, the method further comprises a step S30 of outputting the output data. This allows the data to be further displayed or made available to, for example, clinical staff who may use the data for various purposes. The data may be output by being displayed on a computer screen, or by being transmitted to another location remote from the location where the MRI data are acquired and/or analysed. The data may also be incorporated into a digital file or report concerning the human or animal subject.

The structural information can also be used to classify or identify particular regions or areas of the target object as having a particular type of structure. In an embodiment, the method further comprises determining, on the basis of the output data, information about a microstructure within the target object. Such information could include information about the size of fibres, filaments or channels within a region of the target object, or the density of such features, for example nerve fibres in the brain of a human or animal subject. This information can aid in determining the properties of different regions of the target object, with segmenting the structure of the target object, or classifying different regions. In an embodiment, the method further comprises identifying, on the basis of the information about the microstructure, a structure type of a target region containing the microstructure. For example, regions of white matter in the brain, or other biological tissue types could be identified, or a particular geological formation within a region of rock.

In clinical contexts, the method is particularly valuable when used to identify damaged or diseased tissue. In an embodiment the target object is a human or animal subject, and the identified structure type is associated with a set of one or more pathologies. Optionally, the set of pathologies is predetermined. For example, an operator may determine which pathologies they will compare to the structure type. By comparing the observed structure, and/or information about the microstructure, within a region to known characteristics of particular pathologies, it can be determined whether tissue within that region is exhibiting signs of pathology, disease, or other types of damage or abnormal behaviour. This may provide valuable information for diagnosis of certain conditions, or for assessing the extent of damage and informing treatment strategy.

In an embodiment, the set of pathologies includes one or more of: dementia, or dementia-related tissue damage; a presence of a tumour; a grade of a tumour; a malignancy of a tumour; a presence of tissue damage due to stroke; a presence of stroke lesions; and/or a likelihood of tissue damage due to stroke.

By carrying out these comparisons and identifying tissue structures or potential pathologies as part of the computer-implemented method, the burden on clinical staff can be reduced where the method is applied in a clinical context, thereby allowing more prompt and effective diagnosis and treatment of patients.

The minimum data acquisition to allow estimation of $D_{1,2}$ and a from the QDI model in Eq. 2 requires diffusion signal to be observed at 3 non-equal b-values. Such a data acquisition would include acquisition of signal intensity with low diffusion sensitisation (e.g. $0 \leq b \leq 100$ s $mm^{-2}$) and acquisition of signal intensity at two higher diffusion sensitisations (e.g. $b > 100$ s $mm^{-2}$).

If we consider a QDI acquisition that is analogous to clinical DWI then there is a minimum requirement for 7 diffusion measurements (one $b \approx 0$ s $mm^{-2}$, and 2 higher b-values in 3 diffusion gradient directions in the x, y and z scanner orientations). For a quasi-diffusion tensor imaging (QDTI) acquisition which is analogous to DTI and allows computation of tensor maps there is a requirement for at least 13 diffusion measurements (one $b \approx 0$ s $mm^{-2}$, and 2 higher b-values in 6 non-collinear diffusion gradient directions). Such a minimum acquisition requires considerably fewer measurements than, for example, conventional DKI [Jensen et al., 2005; Jensen & Helpern, 2010], a tensor acquisition that requires a minimum of 31 diffusion measurements (one $b \approx 0$ s $mm^{-2}$, and 2 higher b-values in 15 non-collinear diffusion gradient directions) which represents approximately a 2.4 times greater acquisition time than QDTI (which provides analogous information). This represents a considerable benefit of the QDI technique over conventional DKI as QDTI allows rapid data acquisition in the clinic.

Some results will now be discussed demonstrating the advantages of analysis of NMR data made using the QDI technique, in the specific example of MRI of the human brain.

FIG. 4 shows quasi-diffusion tensor imaging (QDTI) data acquired in 2 minutes on a young, healthy control subject. Data were acquired on a standard 3T Achieva Dual TX MR scanner at St George's University London (SGUL), TE=90 ms, TR=6000 ms, voxel resolution $1.5 \times 1.5 \times 5$ mm$^3$, 8 b=0 s mm$^{-2}$ followed by b=1100 and 5000 s mm$^{-2}$ images in 6 non-collinear diffusion gradient directions. $3 \times 3$ tensors were computed for $D_{1,2}$, $\alpha$ and $H_n$ in each image voxel using the technique described in [Hall & Barrick, 2012]. The tensors were diagonalised and the eigenvalues in each voxel used to compute isotropic and anisotropic maps for each of the $D_{1,2}$, $\alpha$ and $H_n$ maps. Standard terminology is used for describing the isotropic and anisotropic maps of $D_{1,2}$ as mean diffusivity (MD) and fractional anisotropy (FA), respectively. Excellent signal to noise and contrast to noise are apparent despite the exceptionally short acquisition time.

The QDTI technique can provide maps analogous to the conventional DTI maps of MD, FA and the gross orientation of white matter. These are typically shown by Direction Encoded Colour (DEC) maps (red=left/right, green=anterior/posterior; blue=superior/inferior) as shown on the right in FIG. 4. Lower diffusion coefficients are indicative of the tissue microstructural environment providing greater hindrance to diffusing water. QDTI also provides maps of, $\alpha$, a measure of the Gaussianity of diffusion and normalised entropy, $H_n$, a measure relating to how complex the diffusion processes are within an image voxel. In QDI tensor data these measures may be output as isotropic or anisotropic maps.

Tissue contrast in $\alpha$ maps shows white matter values ($\alpha \approx 0.77$) to be lower than grey matter ($\alpha \approx 0.88$) that are in turn lower than cerebrospinal fluid (CSF) ($\alpha \approx 1.0$). Tissue $\alpha$ values indicate that CSF has Gaussian diffusion properties, while grey matter and white matter are characterised by non-Gaussian diffusion. Lower $\alpha$ values in white matter than grey matter indicate that within white matter the step lengths are shorter and waiting times longer, potentially due to greater heterogeneity of the cellular boundaries to diffusion in the tissue microstructural environment within a voxel.

Tissue contrast in $H_n$ maps is similar to diffusional kurtosis maps with high signal in white matter ($H_n \approx 0.62$) and lower values in grey matter ($H_n \approx 0.49$) and CSF ($H_n \approx 0.3$). Tissue $H_n$ values indicate greater complexity of the tissue microstructural environment in white matter than grey matter. As $H_n$ maps computed from QDTI have similar tissue contrast to diffusion kurtosis maps they have immediate potential clinical and research applications.

FIGS. 5 and 6 illustrate the potential of QDTI in clinical application for brain tumour and acute stroke. In all examples the QDTI data were acquired in 2 mins at SGUL.

FIG. 5 shows QDTI maps of low and high grade brain tumours. T1-weighted imaging with gadolinium contrast agent (T1+contrast) are shown with mean diffusivity (MD), $\alpha$ and normalised entropy ($H_n$) that are computed from QDTI data. Brain tumour cases are illustrated for: (a) meningioma, (b) low grade astrocytoma, and (c) high grade glioblastoma.

The low grade tumour cases (FIGS. 5$a$ and 5$b$ depicting a meningioma and low-grade glioma respectively) exhibit an overall increase in MD and low signal in $H_n$. Normalised entropy is decreased compared to white matter due to increased water content in the oedema, less structured tissue in the meningioma, and damaged tissue structure due to infiltrative tumour growth of the glioma. The high grade tumour shows regions of reduced MD and high $H_n$ (FIG. 5$c$). High normalised entropy values represent regions where there is higher cellular density due to rapidly growing tumour (arrows) which closely match areas of angiogenesis detected by T1-weighted contrast enhancement, and surround a core region of increased MD and decreased $H_n$ related to necrosis. The observation of high normalised entropy in high grade tumours is analogous to DKI studies that report high mean kurtosis [Falk et al., 2018]. In particular, DKI studies have shown that high mean kurtosis is representative of high tumour grade and malignancy [Falk et al., 2018]. As QDTI provides analogous information to DKI this means that QDTI provides a rapid technique for identifying tumour grade in the clinic.

FIG. 6 shows QDTI maps of an acute ischemic infarct. Mean diffusivity (MD) and normalised entropy ($H_n$) are shown. Arrows show regions of acute ischemia for which there is a reduction in MD due to the effects of cell-swelling. Normalised entropy is increased in this region providing positive image contrast that clearly delineates the lesion. The observation of high normalised entropy is analogous to DKI studies that report high mean kurtosis in acute stroke lesions [Yin et al., 2018; Zhu et al., 2019]. In particular, DKI studies have shown that stroke lesions with high mean kurtosis may indicate brain tissue that undergoes chronic stroke damage at 1 month follow-up [Yin et al., 2018]. As QDTI provides analogous information to DKI this means that QDTI provides a rapid technique for identifying acute stroke lesions in the clinic and potentially includes valuable information regarding patient recovery.

QDI also offers improvement over fast DKI acquisition and analysis techniques. These improvements include improved tissue contrast-to-noise ratios, increased signal-to-noise ratios and reduced image artefacts. These improvements are described in further detail below using comparisons of mean kurtosis maps from DKI and normalised entropy maps from QDTI. Normalised entropy maps clearly provide analogous tissue contrast to mean kurtosis images.

Quasi-diffusion imaging provides new information that can be used in tractography algorithms to resolve fibre crossing, in particular of white matter or other types of fibrous tissue within the human or animal subject. For example, high angular resolution QDI (HARQDI) offers the possibility of detecting different white matter fibre orientations within voxels where white matter pathways cross over one another by using the dominant principal directions computed from D, $\alpha$ and $H_n$ tensors or their orientation distribution functions. Therefore, in an embodiment, the method further comprises: calculating S25 processed data from the MRI data on the basis of the model, the processed data comprising one or more of a mean diffusivity, a fractional anisotropy, an apparent diffusion coefficient, a normalised entropy, an entropy anisotropy, an apparent diffusion coefficient, the space parameter, or the time parameter; and producing S27 output data by applying a tractography algorithm to the processed data, the output data comprising an orientation of tissue fibres within the human or animal subject. In a similar manner as described above, in such an embodiment, the method may further comprise outputting the output data. This makes the output data available for use by clinical or research staff.

Figure 7:
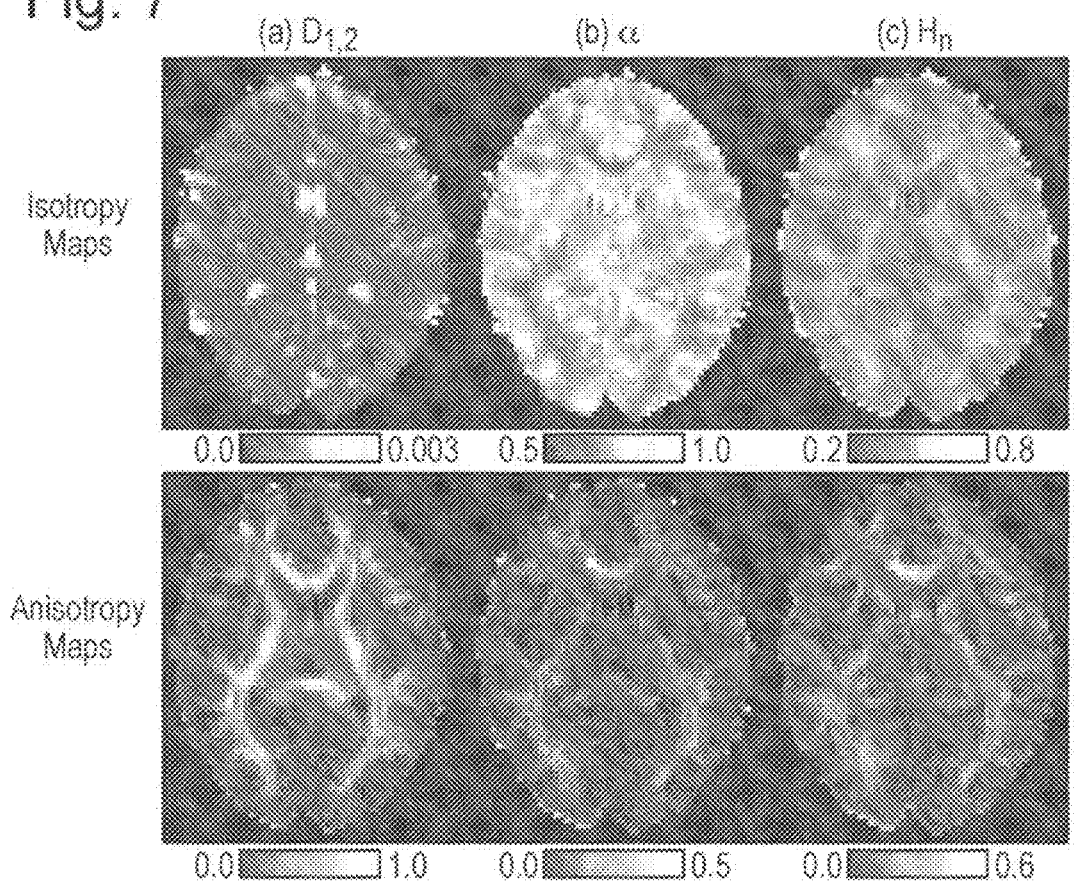
FIG. 7 shows isotropy and anisotropy diffusion parameter maps computed from high-angular resolution quasi-diffusion imaging data.

FIG. 7 shows isotropy and anisotropy maps computed from HARQDI data using a tensor model. The maps are shown through the same axial slices of a young, healthy subjects for (a) $D_{1,2}$, (b) α and (c) $H_n$. The HARQDI data was obtained with 24 diffusion gradient directions and three b-values (b=0, 1000 and 4000 s mm$^{-2}$, 2.5 mm isotropic image resolution, acquisition time 6 min 53 secs using a clinical MRI with standard EPI). The HARQDI data may be used to: (a) compute QDTI maps (FIG. 7), or (b) resolve white matter fibre orientations within a voxel using $D_{1,2}$, a and $H_n$ tensors (FIG. 8).

Figure 8:
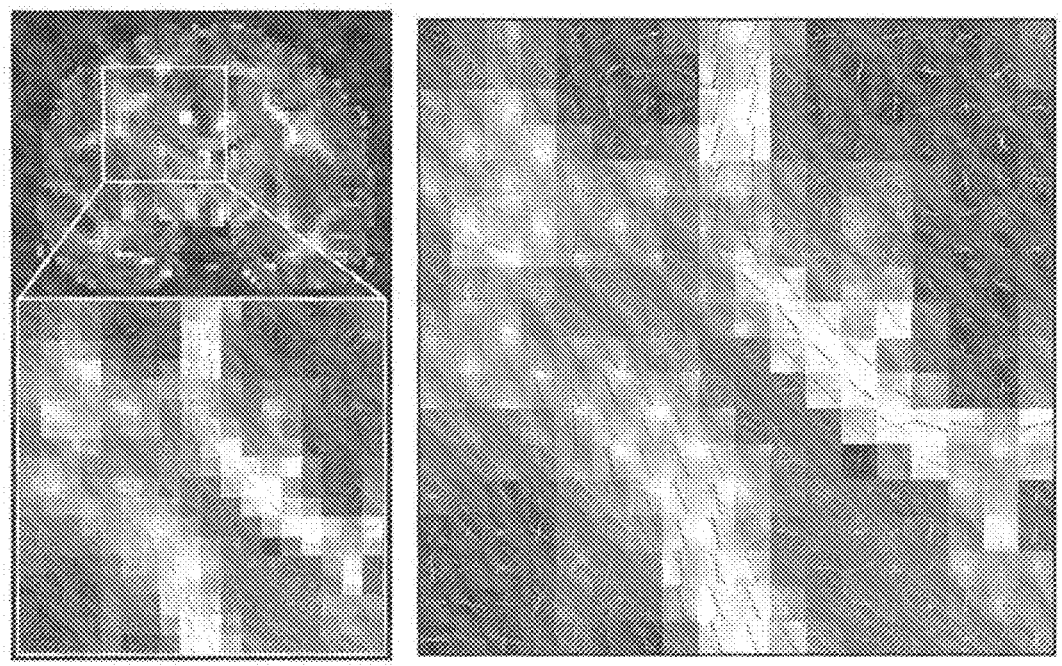
FIG. 8 shows white matter fibre orientations computed from high-angular resolution quasi-diffusion imaging data.

FIG. 8 demonstrates resolution of white matter fibre orientations in a voxel from HARQDI data through the fibre crossing region between the motor pathways and the corpus callosum. White matter fibre orientations through the region of intersection are clearly visible for each white matter pathway. FIG. 8 shows a coronal image of the principal directions of maximum diffusion (i.e. the principal direction of diffusion) and minimum entropy through the motor pathways and corpus callosum. A coronal slice is shown in the top left. In practice, this may be coloured according to a DEC map of the direction of maximum diffusion (i.e. the principal diffusion direction) within each voxel (red=left/right; green=anterior/posterior; blue=superior/inferior). The inset region shows the direction of maximum diffusion through the fibre crossing region. The right panel shows both the direction of maximum diffusion and direction of minimum entropy within the inset region. In the figure, voxel greyscale represents the fractional anisotropy. Fibre orientations would be coloured using the DEC map described above.

Figure 9:
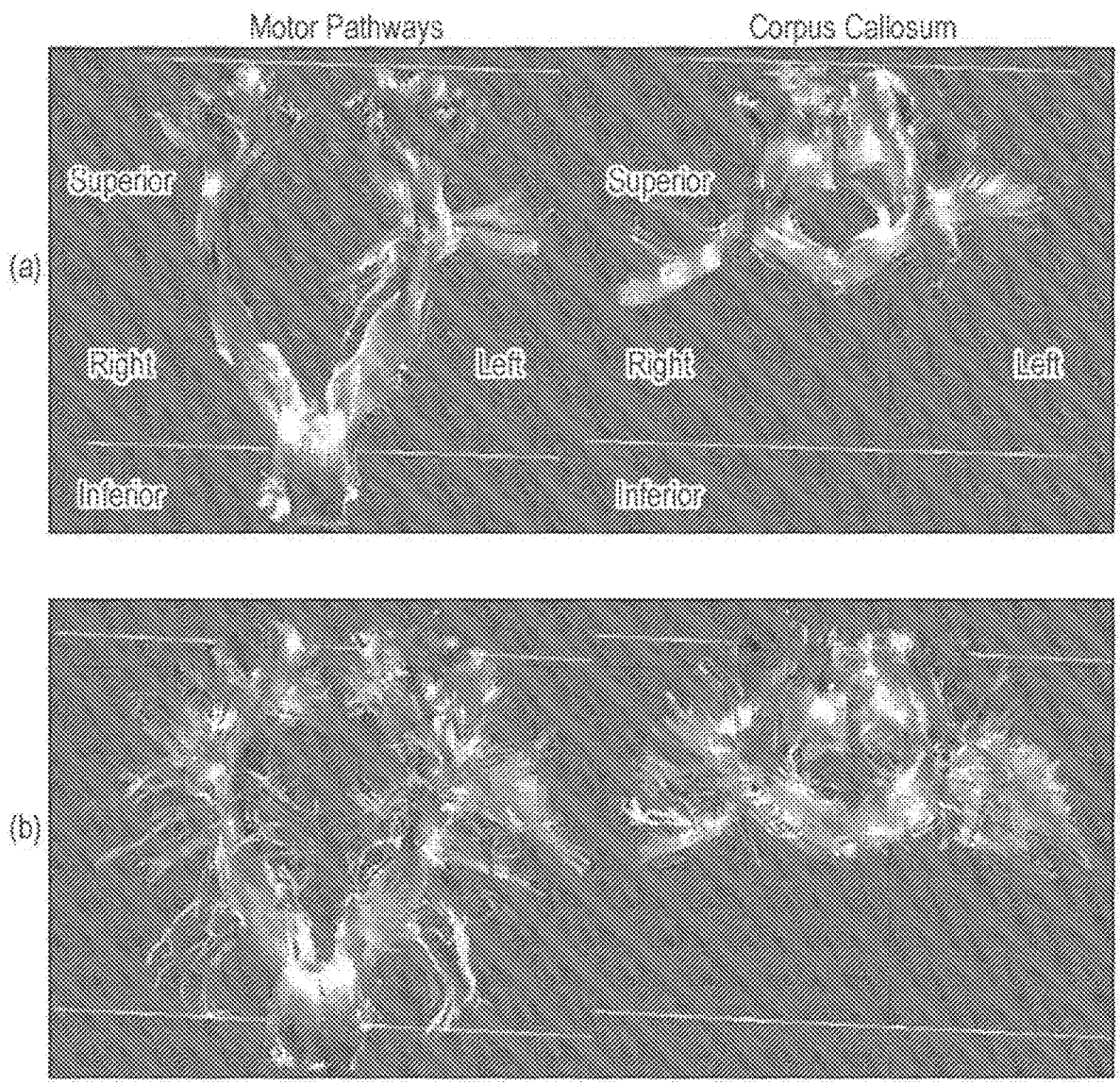
FIG. 9 shows deterministic tractography of the motor pathways and the corpus callosum computed from high-angular resolution quasi-diffusion imaging data.

Tractography algorithms may be applied to QDI data to resolve complex white matter fibre crossings, or other tissue fibre orientation data. FIG. 9 shows an example application of deterministic tractography to HARQDI data of the motor pathways and the corpus callosum to trace white matter pathways. Row (a) shows the white matter pathways that are tracked by following along the direction of maximum diffusion (principal diffusivity direction) alone. Row (b) shows the white matter pathways that are tracked by following both the directions of maximum diffusion and the direction of minimum entropy. Tractography is used to construct the motor pathways and a section of the trunk of the corpus-callosum. This example shows that white matter tractography techniques which follow the principal directions computed from $D_{1,2}$ and $H_n$ tensors improve tractography through brain regions where white matter pathways intersect. In particular, the motor pathways and corpus callosum are shown to pass into all sections of primary motor cortex when following the principal directions computed from $D_{1,2}$ and $H_n$ tensor (FIG. 9b). In practice all tracts are coloured according their orientation (red=left/right; green=anterior/posterior; blue=superior/inferior).

A comparison of fast diffusion kurtosis imaging and quasi-diffusion tensor imaging in clinical cases will now be provided.

The fastest current DKI data acquisition and analysis technique does not provide tensor information [Tietze et al., 2015] and cannot be used to calculate anisotropy maps or resolve white matter orientation distribution functions for fibre tractography. These fast DKI data acquisitions provide similar tissue contrast to QDTI in disease.

Fast DKI data has been acquired in 2 mins 46 secs for brain tumour patients [Tietze et al., 2015], but QDTI has higher contrast-to-noise and higher signal-to-noise ratios than DKI (FIG. 5) despite QDTI being acquired in shorter time. In addition, the QDTI data do not suffer from the black spot artefacts inherent to computation of MK maps as seen in Tietze et al., 2015.

Fast DKI data has also been acquired for stroke patients in 2 mins 10 secs with multiband echo planar imaging (EPI) [Yin et al., 2018], which enables image acquisition to be accelerated by a factor of 2, but is not yet widely implemented on clinical systems. This is in comparison to QDTI data that were acquired at SGUL in 2 mins using conventional EPI on a MRI scanner that was not capable of multiband acquisition (FIG. 6). Use of multiband would allow tensor QDI acquisition in 1 minute or less.

In further embodiments of the method of analysing NMR data, several important insights can be made into the diffusion dynamics described by the quasi-diffusion model. Specifically, QDI parameterises the signal decays by b-value according to the rate of decay, $D_{1,2}$, and the shape of the power law tail, a. The signal decay curve represents the ensemble average of the effects of water diffusion within multiple tissue compartments of varying characteristic size, and with a range of diffusion coefficients. In particular, in some embodiments of the method of analysing NMR data, the step of analysing the NMR data comprises calculating a diffusion spectrum for one or more regions of the target object, the diffusion spectrum of a region being a probability density function (PDF) for values of a diffusion parameter characterising the diffusive behaviour of particles within the region. The diffusion parameter may be an apparent diffusion coefficient, in which case the diffusion coefficient, $D_{1,2}$, and shape exponent, α, of the QDI signal attenuation are transformed to a PDF that provides an intuitive spectral representation of the underlying apparent diffusion coefficients for a given $D_{1,2}$ and α at each image voxel. Thereby, it is possible to transform the signal decay curve to a form which represents a "spectrum" of apparent diffusion coefficients. The diffusion parameter may also be a length scale of a structure within the region of the target object, in which case the signal decay curve is transformed into a form representing a spectrum of compartment sizes within the target object.

The fundamental solution (also known as the Green's function) to the multi-dimensional space-time fractional diffusion equation has been previously derived [Mainardi et al., 2001], and in the special case of quasi-diffusion [Luchko, 2019]. Calculation of the PDFs of diffusing particles in space and time is advantageous because it allows further understanding of the diffusion dynamics modelled by QDI by providing apparent diffusion coefficient or length scale information about the diffusion dynamics. For QDI the shape of the Green's function is dependent on a but not $D_{1,2}$.

Figure 12A:
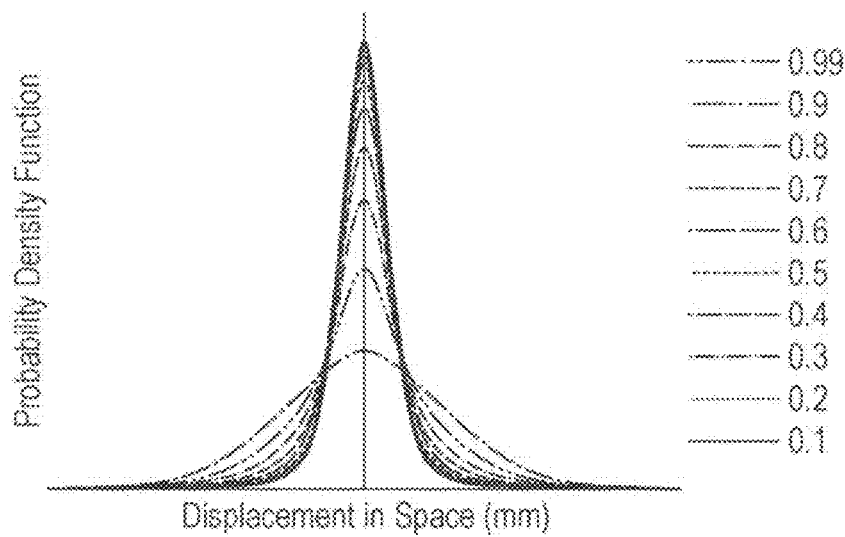
FIG. 12 shows the family of Green's functions, NMR signal decay curve and their Laplace transforms in QDI for an arbitrarily chosen diffusion coefficient $D_{1,2}$.

Green's functions for the quasi-diffusion model are shown in FIG. 12a, where the PDFs for 3-dimensional diffusion for x at a diffusion time, $t=\overline{\Delta}$ is illustrated. FIG. 12a shows for α=0.99 that the PDF is almost Gaussian. As a decreases from 0.99 to 0.1 the PDFs deviate further from a Gaussian PDF and become more peaked (i.e. leptokurtic). The effect of altering the diffusion coefficient, $D_{1,2}$, would be to narrow or broaden these distributions, but would maintain the same shape. The PDFs illustrated in FIG. 12a provide a direct analogy to diffusional kurtosis imaging (DKI), [Jensen et al., 2005; Jensen et al., 2010] where the PDFs are assumed to represent non-Gaussian diffusion and become more leptokurtic as diffusion deviates further from a Gaussian distribution. Although DKI assumes that the PDFs of diffusing particles will follow such a theoretical relationship it is not possible to compute the shape of the PDFs from the DKI representation that is currently used [Jensen et al., 2005; Jensen et al., 2010] to describe the dMRI signal attenuation.

FIG. 12a indicates that the same physical interpretation of diffusion signal attenuation in QDI may be employed as for that assumed to be represented by DKI. FIG. 12a also indicates one of the key differences between QDI and current dMRI signal representation techniques (such as DKI). Specifically, in the preferred embodiment QDI is based on the CTRW model of diffusion and may be used to provide physical information regarding the diffusion dynamics within a voxel, whereas techniques that simply represent the diffusion decay curve as an arbitrary function cannot provide PDFs of the diffusion process.

FIG. 12a may be used to infer the behaviour of diffusing particles at different length scales. In particular, shorter step lengths in the random walk are more likely as α decreases. Although not shown in FIG. 12a, at a sufficiently long length scale the family of curves inverts, indicating that the tails of the PDF exhibit greater likelihood of longer step lengths as α decreases. This is intuitively reasonable as increased complexity of the diffusion environment would lead to greater likelihood of shorter step lengths, but with a small chance of longer step lengths as the particles diffuse between traps.

Figure 12B:
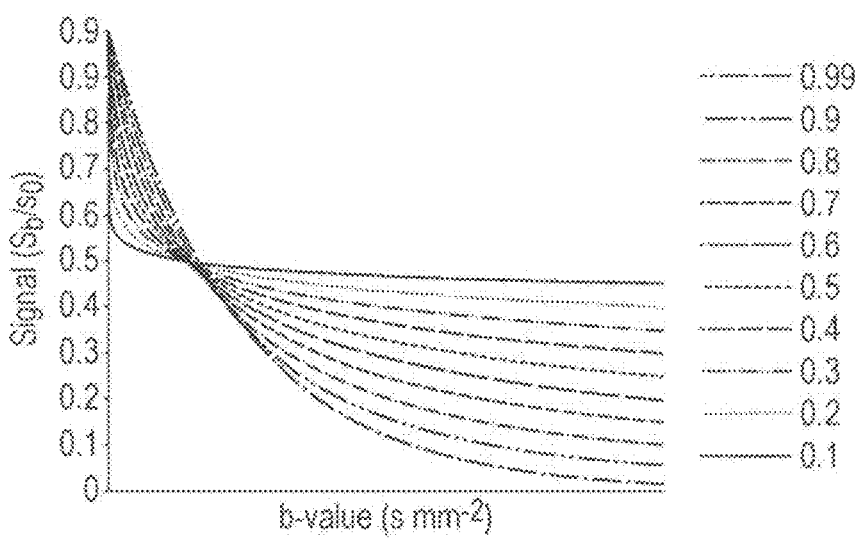

In some embodiments, calculating the diffusion spectrum comprises taking an integral transform of the model of the diffusive behaviour of particles within the target object, wherein optionally the integral transform is a Laplace transform or a Fourier transform. The Laplace transform for the quasi-diffusion model in NMR may be directly calculated from the QDI signal decay curve (Eq. 2, FIG. 12b) to provide a probability density function (PDF) of Apparent Diffusion Coefficients (ADCs in mm$^2$s$^{-1}$). The mathematical description of the Laplace transform for the type of Mittag-Leffler function represented by [Eq. 2] has been previously derived [Berberan-Santos, 2005]. Specifically, the diffusion signal attenuation in [Eq. 2] is described by the Mittag-Leffler function, $E_\alpha(z)$, $$E_\alpha(z) = \sum_{k=0}^{\infty} \frac{z^k}{\Gamma(\alpha k + 1)} \quad [5]$$

where $z=-(bD_{1,2})^\alpha$ and b is the diffusion-weighting in s mm$^{-2}$, $D_{1,2}$ is the diffusion coefficient in mm$^2$s$^{-1}$, and α is the fractional (i.e. shape) exponent of the diffusion signal attenuation. The Mittag-Leffler function in [Eq. 5] may be rewritten in the form $E_\alpha(-x^\alpha)$ where $x=bD_{1,2}$. The Laplace transform for $E_\alpha(-x^\alpha)$ has been previously derived [Berberan-Santos, 2005] and the integral representation is given by, $$E_\alpha(-x^\alpha) = \frac{\sin(\alpha\pi)}{\pi} \int_0^\infty \frac{k^{\alpha-1}}{1 + 2k^\alpha \cos(\alpha\pi) + k^{2\alpha}} e^{-xk} \, dk \quad [6]$$

which provides the Laplace transform pairs, $$E_\alpha(-x^\alpha) \overset{\mathcal{L}}{\leftrightarrow} \frac{1}{\pi} \frac{\sin(\alpha\pi)k^{\alpha-1}}{1 + 2k^\alpha \cos(\alpha\pi) + k^{2\alpha}}, \quad [7]$$

for 0<α<1. By substitution of $x=bD_{1,2}$ into [Eq. 6] we have, $$E_\alpha(-(bD_{1,2})^\alpha) = \frac{\sin(\alpha\pi)}{\pi} \int_0^\infty \frac{k^{\alpha-1}}{1 + 2k^\alpha \cos(\alpha\pi) + k^{2\alpha}} e^{-bD_{1,2}k} \, dk \quad [8]$$

which is a transform between the QDI signal attenuation and a PDF of ADCs. [Eq. 8] indicates that the non-Gaussian QDI signal attenuation can be decomposed into a distribution of mono-exponential decay curves, and consequently that quasi-diffusion dynamics can be represented as a distribution of Gaussian diffusivities.

The Laplace transform of the QDI signal decay curve provides several important additions to QDI in terms of interpreting the $D_{1,2}$ and a data, and further supports the utility of QDI for application in target objects with complex structures, such as tissues of humans or animals. The Laplace transform of the dMRI quasi-diffusion equation allows representation of $D_{1,2}$ and α parameters obtained by QDI as a PDF of ADCs in units of mm$^2$s$^{-1}$. These apparent diffusion coefficients characterize the diffusive behaviour of particles. Thus for a particular region, e.g. an image voxel, instead of the overall diffusion being represented by a characteristic $D_{1,2}$ and α pair, it can be intuitively visualized as a continuous spectrum of ADCs that exist within the sample.

The concept of creating an ADC spectrum from the dMRI decay curve was first introduced by Yablonskiy et al., [2003] where a Gaussian PDF was assumed. The application of an integral transform from the signal decay curve to a probability distribution of ADCs provides an intuitive visualization of the ensemble diffusion processes within an image voxel in terms of a ranges of ADCs that may relate to specific length scales [Yablonskiy et al., 2003; Magin et al., 2012]. Changes within specific parts of the ADC spectrum have been related to pathological changes in recent studies that have assumed a gamma variate distribution function for the shape of the ADC spectrum [Borlinhas et al., 2019, Oshio et al., 2014]. However, in all these studies there has been a need to make an assumption as to the functional form of the probability distribution without supporting evidence.

In contrast, QDI provides the form of the PDF directly from the Laplace transform of the QDI decay curve. Therefore, there is a one-to-one mapping (i.e. the Laplace transform pair) between the QDI signal attenuation and the spectrum of Gaussian ADCs which form the observed non-Gaussian diffusion signal attenuation within an image voxel. This provides further theoretical evidence indicating that the non-Gaussian diffusion dynamics described by the quasi-diffusion model are anomalous but not exotic, and represent a spectrum of Gaussian diffusivities.

It was described above that the QDI form for diffusion signal decay provides an exceptionally stable and excellent fit to the observed data. Adding the further feature of calculating the diffusion spectrum allows ADC spectra to be obtained using acquisition times that are considerably shorter than those currently used for gamma variate analysis in dMRI. In particular, the QDI method offers a fast image acquisition for obtaining voxel ADC spectra that can be feasibly applied in the clinical arena. A further application of the quasi-diffusion model could include Diffusion Spectrum Imaging (DSI) [Wedeen et al., 2005] for which the signal decay curve is obtained with very high numbers of b-values. Use of Fourier transform of the QDI decay curve would enable the possibility of much reduced DSI data acquisitions.

In summary, using QDI permits the computation of Laplace transform pairs (or other integral transforms) between the diffusion signal attenuation and an ADC spectrum, and so provide a consistent model of diffusion dynamics and ADC spectra that enables complex models of dMRI to be developed with greatly reduced data acquisition overheads.

Figure 12C:
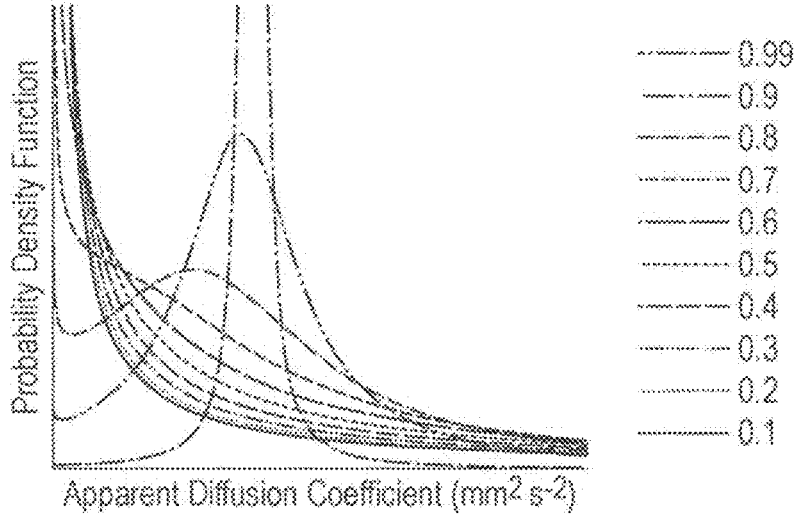

Examples of the possible variations in shape of the PDFs (i.e. diffusion spectra) obtained by Laplace transform of the QDI signal attenuation curve are shown in FIG. 12c for different values of a between 0.1 and 0.99 at an arbitrary $D_{1,2}$. The shape of the Laplace transform provides the spectrum of apparent diffusion coefficients that contribute to an observed $D_{1,2}$ and $\alpha$. At an a close to unity (e.g. $\alpha$=0.99 in FIG. 12c the PDF becomes more symmetrical and Gaussian-like in appearance, eventually approaching that of a Dirac delta function. This then represents a single ADC where the diffusion dynamics within the structure being studied are Gaussian with no boundaries that hinder or restrict diffusing particles. As a decreases (0.9 to 0.7) the PDF broadens out to a non-Gaussian shape that includes significant contributions at low ADCs which represents the characteristics of restricted diffusion. For $\alpha$<0.7 the PDF shape alters continuously and smoothly to an inverse power law and at low a to a hyperbolic curve. It should be noted that in practice for dMRI in brain tissue, typical values for $\alpha$ are in the range $1 \geq \alpha > 0.7$.

This method has several advantages over other techniques that aim to probe the structural and diffusion characteristics of a target object: (1) the Laplace transform pairs are well defined, (2) long dMRI acquisition sequences with different q or $\overline{\Delta}$ are not required. In addition, it is possible to obtain the PDF of other physical characteristics, for example, the length scales of the structure of the target object (e.g. human tissue microstructure). For instance, the pore size length scale is fundamental to the effects of diffusion restriction in the region, e.g. an image voxel. An example is calculation of the length scale, l, in μm for each Gaussian ADC, $D_G$, within the ADC spectrum according to $$l = \sqrt{2\overline{\Delta} D_G}$$

to provide a PDF of structural length scales. The characteristics of these diffusion spectra, being PDFs of diffusion coefficients or structural length scales, can be calculated from the moments of the PDFs. These provide, for example, the mean, variance, standard deviation, coefficient of variation, skew and kurtosis of the spectra and can be computed on a voxel-by-voxel basis, or within regions of interest. Calculation of the moments of the PDFs creates a completely new set of images of target objects that relate to physical measures that could have enhanced diagnostic capability compared to current methods. Furthermore, computation of the moments allows the QDI method to provide physical measurements of the diffusion process, rather than just a representation of the data.

Several example ADC spectra have been calculated using the QDI method and are shown in FIGS. 13-16 computed from QDTI data. The Laplace transform of the axial (i.e. along-axon) and radial (i.e. axonal or pore cross-section) measures within each image voxel was computed to provide a spectrum of ADCs contributing to the diffusion signal attenuation at each image voxel.

Figure 13A:
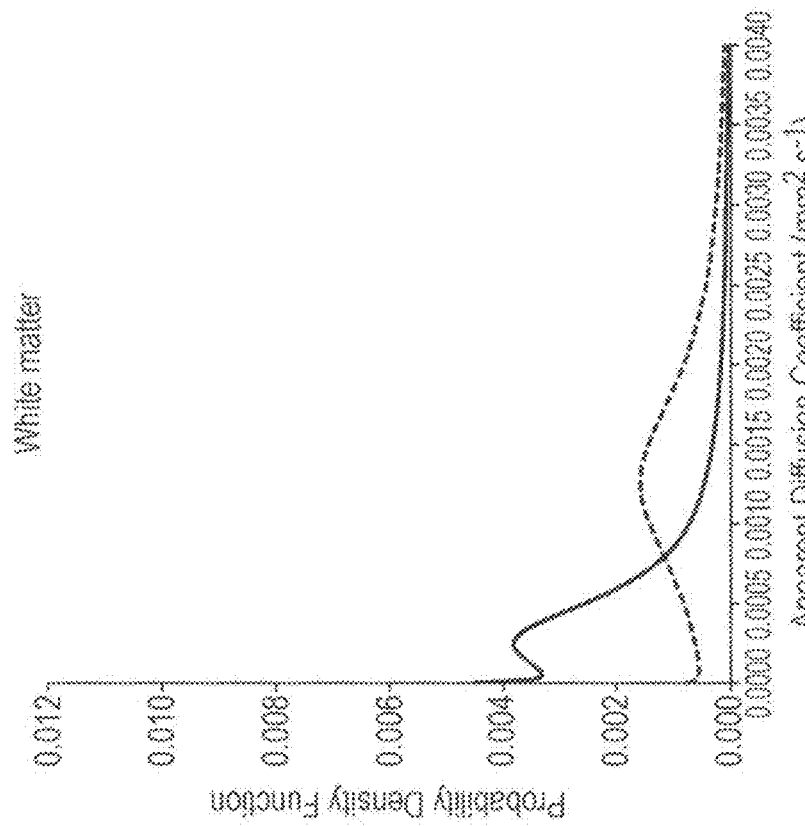
FIG. 13 shows diffusion spectra of a dMRI decay curve in QDI calculated for single voxels within the brain of a healthy subject.
Figure 13B:
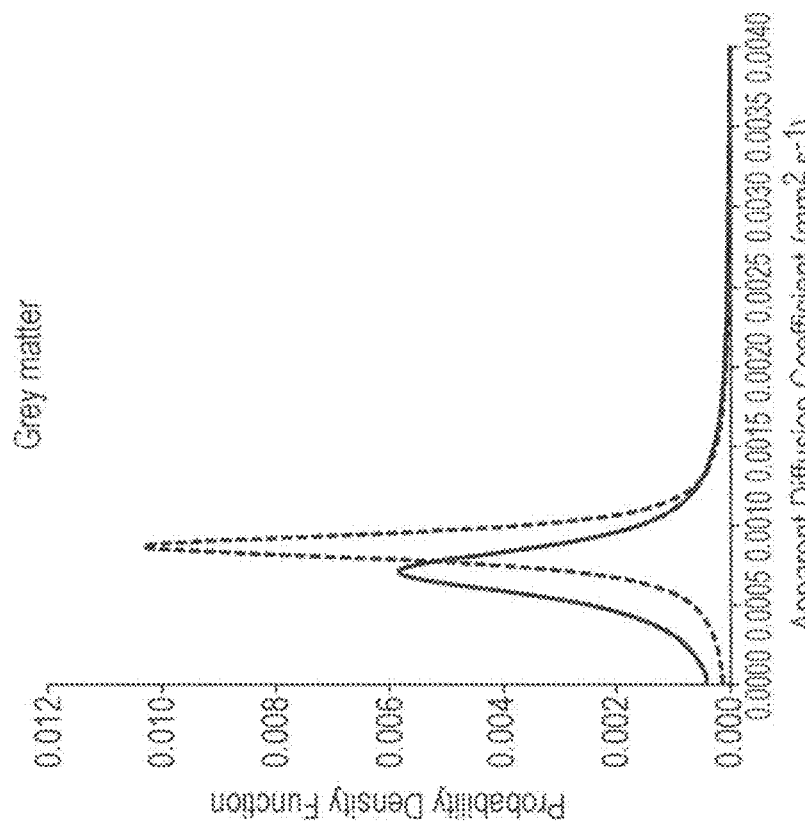

FIG. 13 shows axial and radial ADC spectra obtained from single voxels in healthy grey matter, healthy white matter, and cerebrospinal fluid (CSF). All spectra were obtained from a young, healthy subject. Grey matter spectra show that the diffusion is primarily isotropic with narrow distributions of ADCs centred around $0.8 \times 10^{-3}$ mm$^2$s$^{-1}$ contributing to the axial and radial diffusion signals. White matter spectra are highly anisotropic with broad distributions of axial ADCs centred around $1.40 \times 10^{-3}$ mm$^2$s$^{-1}$ and radial ADCs predominately below $0.5 \times 10-3$ mm$^2$s$^{-1}$. The CSF ADC distributions are both narrow and centred at approximately $3.0 \times 10^{-3}$ mm$^2$s$^{-1}$. Spectra such as these can be computed at each image voxel and also in each diffusion direction individually.

Characteristic length scales are shown as an effective pore radius image in FIG. 14 and indicate that the effective radius of white matter axonal structures is approximately 2 μm. The axonal radius of 2 μm computed from QDI is similar to effective axon radii measurements reported by [Veraart et al., 2020], the key difference being that the QDI data illustrated in FIG. 14 was acquired in less than 7 minutes on a clinical MR scanner.

Figure 15A:
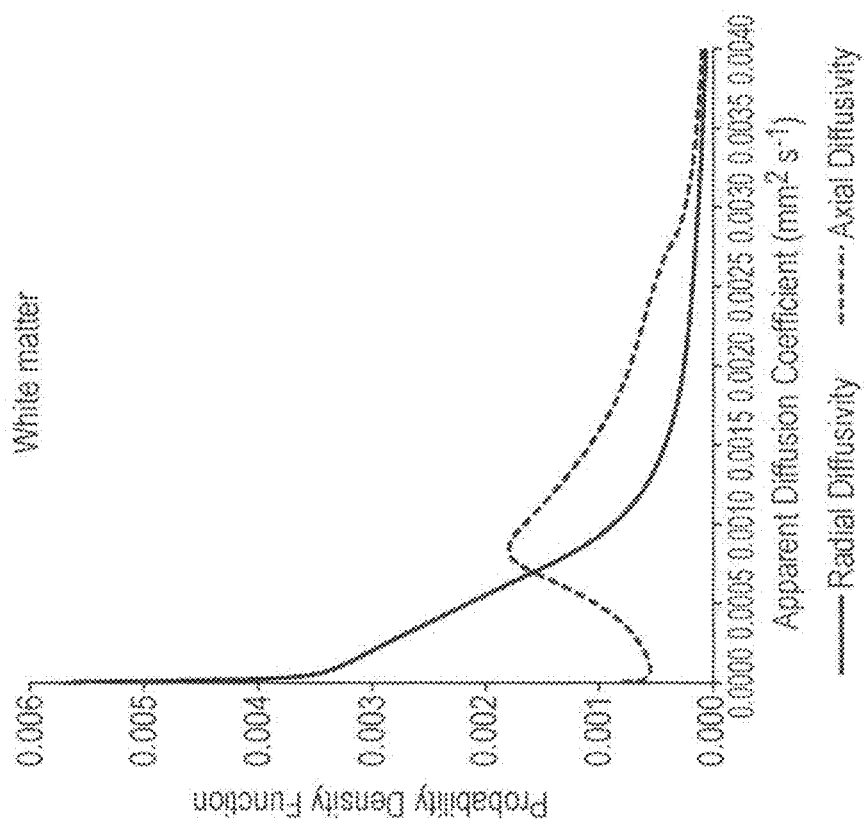
FIG. 15 shows diffusion spectra of a dMRI decay curve in QDI calculated for whole brain tissue within the brain of a healthy subject.
Figure 15B:
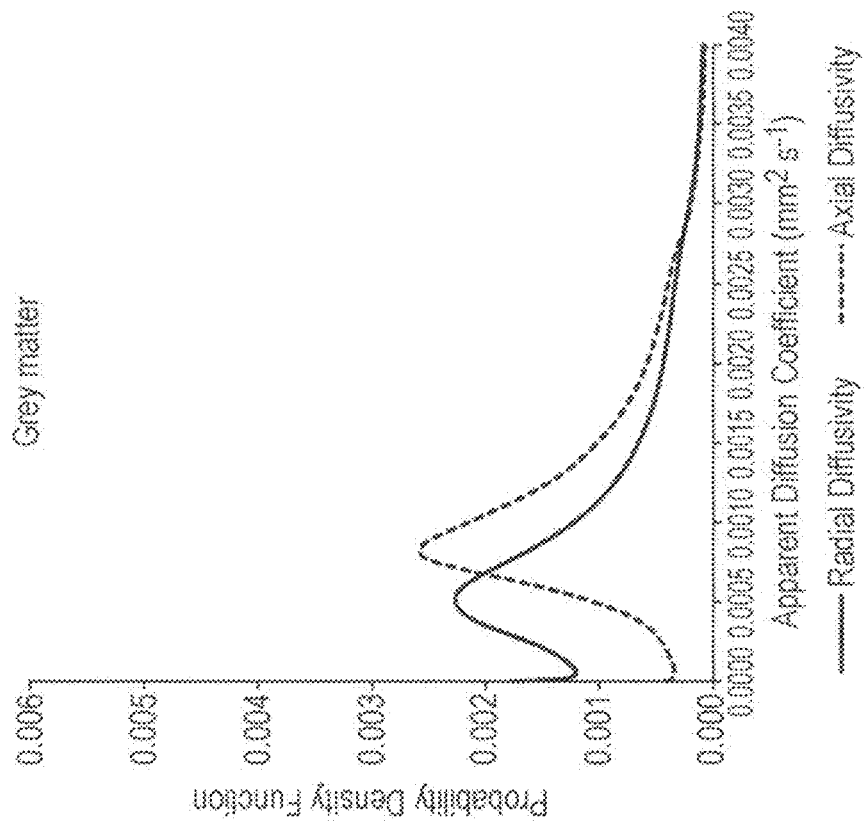

Average ADC spectra can be calculated within regions of interest from dMRI data. These regions of interest can be any size or shape. FIG. 15 shows average ADC spectra computed for axial and radial QDI measures from whole brain tissue segmentations of (a) grey matter and (b) white matter. All spectra were obtained from a young, healthy subject within regions of interest that were defined to include voxels with greater than or equal to 95% tissue probability. These results show that the average spectra are broader in each tissue type and provide a more general spectrum of the possible ADCs that contribute to the QDI signal decay throughout the whole brain. The small amount of anisotropy observed between axial and radial ADC spectra in grey matter is likely explained by tissue complexity at the boundary between grey and white matter, where the highly directional white matter meets the isotropic grey matter.

To illustrate the potential for clinical application of the diffusion spectra, for example using the Laplace transform of the QDI signal attenuation, three brain tumour cases were considered. These cases are the same brain tumour examples that have been previously shown in FIG. 5 and include a grade I meningioma, a grade II astrocytoma (i.e. a low grade glioma, LGG) and grade IV glioblastoma (i.e. a high grade glioma, HGG). Average ADC spectra for axial and radial QDI signal attenuation in brain tumour regions of interest within (i) surrounding oedema and (ii) tumour core are shown in FIG. 16. Axial and radial ADC spectra are shown for patient cases with (a) meningioma, (b) grade II astrocytoma, and (c) grade IV glioblastoma. Regions of interest (ROIs) were manually drawn to define the tumour cores and oedema. The core in the meningioma and glioblastoma were defined from the T1 contrast enhancing region, and their oedema as the surrounding hyperintense FLAIR region. The whole of the hyperintense FLAIR region was defined as the LGG core. These results demonstrate how the ADC spectral characteristics can provide interpretation of pathological changes and tissue-type classification.

The oedema in the meningioma is within white matter, and the oedema ADC spectra are compared to the white matter axial and radial ADC spectra shown in FIG. 15. In FIG. 16(a)(i) the meningioma exhibits high anisotropy, but with a comparative shift towards higher average ADCs with Gaussian-like spectra for both axial and radial components. The presence of spectral anisotropy within the meningioma core (FIG. 16(a)(ii)) is consistent with the structural characteristics of some meningiomas that have a fibrous element with fascicular structures and diffusion anisotropy.

Gliomas grow and infiltrate within the white matter architecture, and in the early stages of LGG growth there is a significant proportion of normal brain tissue within the abnormality region depicted by standard MRI. Compared to white matter, the LGG axial ADC spectrum exhibits a shift towards a more Gaussian PDF, and the radial ADC spectrum shows a shoulder of higher diffusivities than white matter (FIG. 16(b)(i)). This is consistent with the loss of anisotropic WM structures within the lesion, and a more fluid environment, as revealed by signal increases on the T2-weighted FLAIR image. The HGG shows further progression of these characteristics. The FLAIR region of oedema shows a reduction of anisotropy at the lowest ADCs and overall shifts of the axial and radial PDFs towards higher diffusion (FIG. 16(c)(i)). This oedema will be a mix of tumour infiltration and oedematous brain, and has very distinct characteristic PDFs compared to that of the meningioma which is purely brain oedema. Within the core of the HGG there is a large shift of the maximum radial ADC towards the axial ADC maximum, indicating further loss of tissue structure compared to the LGG (FIG. 16(c)(ii)). Nevertheless, anisotropy is still present in the PDFs and is consistent with MR spectroscopy data from this tumour that shows the presence of NAA (a marker of neuronal structures) in the tumour core.

The PDFs that have been derived from these tumour regions show different spectral characteristics for pure oedema compared to infiltrative oedema, as well as differences between tumour types. In the current analysis the PDFs have been derived on the basis of manually delineated tissue regions derived from conventional clinical images. It is clear that specific ADC spectral characteristics derived from QDI data could be used to label tissue regions according to their diffusion characteristics as an alternative segmentation of normal and abnormal tissue according to standard MRI, as shown previously for Magnetic Resonance Spectroscopy [Raschke et al., 2019], but at the higher spatial resolution of QDI.

Figure 17:
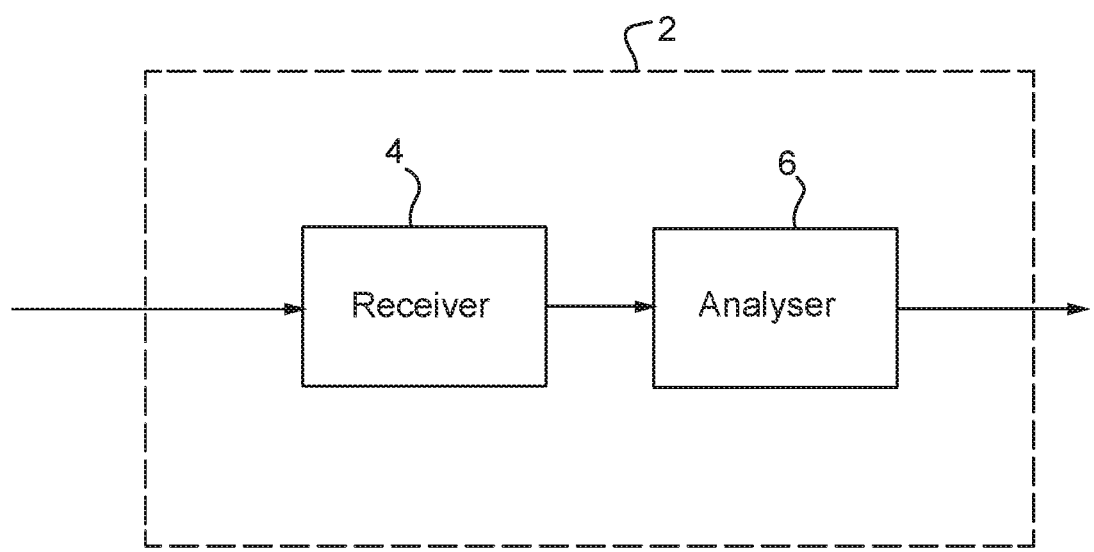
FIG. 17 shows an apparatus according to an embodiment.

The methods of analysing MRI data provided herein may be implemented using an apparatus 2 for analysing NMR data of a target object, as shown in FIG. 17. The apparatus 2 comprises receiving means 4 configured to receive NMR data of the target object, and analysis means 6 configured to analyse the NMR data using a model of the diffusive behaviour of particles within the target object, wherein the model includes a time parameter and a space parameter, the time parameter describing temporal characteristics of the diffusive behaviour of particles in the model and the space parameter describing spatial characteristics of the diffusive behaviour of particles in the model, and the model is constrained such that the value of the time parameter and the value of the space parameter are related according to a correlation function. The apparatus 2 may be further modified to carry out analysis in a manner analogous to any of the variations of the analysis method discussed above.

Further, a computer program may be used to implement the method of analysing MRI data described above, wherein the computer program comprises instructions which, when the program is executed by a computer, cause the computer to carry out the method. Similarly, a computer-readable medium may be used to store the computer program, or to store instructions which, when executed by a computer, cause the computer to carry out the method.

REFERENCES

Abramson R G, Burton K R, Yu J P, Scalzetti E M, Yankeelov T E, Rosenkrantz A B, Mendiratta-Lala M, Bartholmai B J, Ganeshan D, Lenchik L, Subramaniam R M (2015). Methods and challenges in quantitative imaging biomarker development. Academic Radiology, 22(1): 25-32.

Alexander D C (2008). A general framework for experiment design in diffusion MRI and its application in measuring direct tissue-microstructure features. Magnetic Resonance in Medicine 60(2):439-448.

Alexander D C, Hubbard P L, Hall M G, Moore E A, Ptito M, Parker G J, Dyrby T B (2010). Orientationally invariant indices of axon diameter and density from diffusion MRI. Neuroimage 52(4):1374-89.

Assaf Y, Basser P J (2005). Composite hindered and restricted model of diffusion (CHARMED) M R imaging of the human brain. Neuroimage 27(1):48-58. Assaf Y, Blumenfeld-Katzir T, Yovel Y, Basser P J (2008). AxCaliber: a method for measuring axon diameter distribution from diffusion MRI. Magnetic Resonance in Medicine 59(6):1347-54.

Benitez A, Jensen J H, Falangola M F, Nietert P J, Helpern J A (2018). Modelling white matter tract integrity in aging with diffusional kurtosis imaging. Neurobiology of Aging 70:265-275.

Berberan-Santos M N (2005). Properties of the Mittag-Leffler Relaxation Function, Journal of Mathematical Chemistry, 38(4): 629-635.

Bonet-Carne E, Johnston E, Daducci A, Jacobs J G, Freeman A, Atkinson D, Hawkes D J, Punwani S, Alexander D C, Panagiotaki E (2019). VERDICT-AMICO: Ultrafast fitting algorithm for non-invasive prostate microstructure characterization. NMR in Biomedicine 32(1):e4019.

Borlinhas F, Loução R, C Conceigção R, Ferreira H A (2019). Gamma Distribution Model in the Evaluation of Breast Cancer Through Diffusion-Weighted MRI: A Preliminary Study. Journal of Magnetic Resonance Imaging. 50(1):230-238.

Dynkin E B (1965). Markov Processes, Volume 1, Springer.

Falk Delgado A, Nilsson M, van Westen D, Falk Delgado A (2018). Glioma Grade Discrimination with M R Diffusion Kurtosis Imaging: A Meta-Analysis of Diagnostic Accuracy. Radiology, 287(1):119-127.

Farquharson S, Tournier J D, Calamante F, Fabinyi G, Schneider-Kolsky M, Jackson G D, Connelly A (2013). White matter fiber tractography: why we need to move beyond DTI. Journal of Neurosurgery 118(6):1367-77.

Gong N J, Chan C C, Leung L M, Wong C S, Dibb R, Liu C (2017). Differential microstructural and morphological abnormalities in mild cognitive impairment and Alzheimer's disease: Evidence from cortical and deep gray matter. Human Brain Mapping, 38(5):2495-2508.

Hall M G and Barrick T R (2012). Two-step anomalous diffusion tensor imaging. NMR in Biomedicine. 25(2): 286-94.

Ingo C, Barrick T R, Webb A G, Ronen I (2017), Accurate Pade global approximations for the Mittag-Leffler function, its inverse, and its partial derivatives to efficiently compute convergent power series. International Journal of Applied and Computational Mathematics 3 (2), 347-362.

Ingo C, Magin R L, Colon-Perez L, Triplett W, Mareci T H (2014). On random walks and entropy in diffusion-weighted magnetic resonance imaging studies of neural tissue. Magnetic Resonance Medicine, 71(2):617-27.

Ingo C, Sui Y, Chen Y, Parrish T B, Webb A G, Ronen U (2015). Parsimonious continuous time random walk models and kurtosis for diffusion in magnetic resonance of biological tissue. Frontiers In Physics 3, 11.

Jelescu I O, Veraart J, Adisetiyo V, Milla S S, Novikov D S, Fieremans E (2015). One diffusion acquisition and different white matter models: how does microstructure change in human early development based on WMTI and NODDI? Neuroimage 15; 107:242-256.

Jelescu I O, Veraart J, Fieremans E, Novikov D S (2016). Degeneracy in model parameter estimation for multicompartmental diffusion in neuronal tissue. NMR in Biomedicine 29(1):33-47.

Jensen J H, Helpern J A. MRI quantification of non-Gaussian water diffusion by kurtosis analysis (2010). NMR in Biomedicine. 23(7):698-710.

Jensen J H, Helpern J A, Ramani A, Lu H, Kaczynski K (2005). Diffusional kurtosis imaging: the quantification of non-Gaussian water diffusion by means of magnetic resonance imaging. Magnetic Resonance in Medicine 53(6): 1432-40.

Jeurissen B, Leemans A, Jones D K, Tournier J D, Sijbers J. (2011). Probabilistic fiber tracking using the residual bootstrap with constrained spherical deconvolution. Human Brain Mapping 32(3):461-79.

Jeurissen B, Tournier J D, Dhollander T, Connelly A, Sijbers J (2014). Multi-tissue constrained spherical deconvolution for improved analysis of multi-shell diffusion MRI data. Neuroimage 103:411-426.

Jurlewicz A, Kernb P, Meerschaert M M, Scheffler H-P (2012). Fractional governing equations for coupled random walks. Computers and Mathematics with Applications 64:3021-3036.

Klages R, Radons G, Sokolov I M (editors) (2008). Anomalous Transport: Foundations and Applications, Wiley-VCH Verlag GmbH & Co.

Lampinen B, Szczepankiewicz F, Mårtensson J, van Westen D, Sundgren P C, Nilsson M (2017). Neurite density imaging versus imaging of microscopic anisotropy in diffusion MRI: A model comparison using spherical tensor encoding. Neuroimage 147:517-531.

Luchko Y, (2019). Subordination principles for the multidimensional space-time-fractional diffusion-wave equation. Theory of Probability and Mathematical Statistics 98: 127-147.

Magin R L, Abdullah O, Baleanu D, Zhou X J (2008). Anomalous diffusion expressed through fractional order differential operators in the Bloch-Torrey equation. Journal of Magnetic Resonance, 190(2):255-70.

Magin R L, Rawash Y Z, Berberan-Santos M N (2012). Analyzing anomalous diffusion in NMR using a distribution of rate constants, Chapter 22 pp. 263-274 in Fractional Dynamics and Control, D. Baleanu, J. A. T. Machado and A. C. J. Luo (editors), Springer, London.

Mainardi F, Luchko Y, Pagnini G (2001). The fundamental solution of the space-time fractional diffusion equation, Fractional Calculus and Applied Analysis, 4(2): 153-192.

Metzler R and Klafter J (2000) The Random Walk's Guide to Anomalous Diffusion: A Fractional Dynamics Approach. Physics Reports, 339, 1-77.

Novikov D S, Veraart J, Jelescu I O, Fieremans E (2018). Rotationally-invariant mapping of scalar and orientational metrics of neuronal microstructure with diffusion MRI. Neuroimage 174:518-538.

Oshio K, Shinmoto H, Mulkern R V (2014). Interpretation of diffusion M R imaging data using a gamma distribution model. Magnetic Resonance in Medicine 13(3):191-5.

Panagiotaki E, Chan R W, Dikaios N, Ahmed H U, O'Callaghan J, Freeman A, Atkinson D, Punwani S, Hawkes D J, Alexander D C. Microstructural characterization of normal and malignant human prostate tissue with vascular, extracellular, and restricted diffusion for cytometry in tumours magnetic resonance imaging. Investigative Radiology 50(4):218-27.

Panagiotaki E, Walker-Samuel S, Siow B, Johnson S P, Rajkumar V, Pedley R B, Lythgoe M F, Alexander D C (2014). Noninvasive quantification of solid tumor microstructure using VERDICT MRI. Cancer Research 74(7): 1902-12.

Praet J, Manyakov N V, Muchene L, Mai Z, Terzopoulos V, de Backer S, Torremans A, Guns P J, Van De Casteele T, Bottelbergs A, Van Broeck B, Sijbers J, Smeets D, Shkedy Z, Bijnens L, Pemberton D J, Schmidt M E, Van der Linden A, Verhoye M (2018). Diffusion kurtosis imaging allows the early detection and longitudinal follow-up of amyloid-β-induced pathology. Alzheimer's Research & Therapy, 10(1):1.

Raschke F, Barrick T R, Jones T L, Yang G, Ye X, Howe F A (2019). Tissue-type mapping of gliomas. Neuroimage Clin. 21:101648.

Tietze A, Hansen M B, Østergaard L, Jespersen S N, Sangill R, Lund T E, Geneser M, Hjelm M, Hansen B (2015). Mean Diffusional Kurtosis in Patients with Glioma: Initial Results with a Fast Imaging Method in a Clinical Setting. American Journal of Neuroradiology, 36(8):1472-8.

Veraart, J, Nunes D, Rudrapatna U, Fieremans E, Jones D K, Novikov D S, Noam Shemesh (2020). Noninvasive quantification of axon radii using diffusion MRI. eLife Journal, 9:e49855.

Wedeen V J, Hagmann P, Tseng W Y, Reese T G, Weisskoff R M (2005). Mapping complex tissue architecture with diffusion spectrum magnetic resonance imaging. Magnetic Resonance in Medicine 54(6):1377-86.

Yablonskiy D A, Bretthorst G L, Ackerman J J H (2003). Statistical Model for Diffusion Attenuated M R Signal, Magnetic Resonance in Medicine 50(4): 664-669.

Yin J, Sun H, Wang Z, Ni H, Shen W, Sun P Z (2018). Diffusion Kurtosis Imaging of Acute Infarction: Comparison with Routine Diffusion and Follow-up M R Imaging. Radiology 287(2):651-657.

Zhu L H, Zhang Z P, Wang F N, Cheng Q H, Guo G (2019). Diffusion kurtosis imaging of microstructural changes in brain tissue affected by acute ischemic stroke in different locations. Neural Regeneration Research 14(2):272-279.

The invention claimed is:
1. A method comprising:
scanning a target object using a magnetic resonance scanner to generate nuclear magnetic resonance, NMR, data of the target object;
receiving, by a computer configured to execute instructions stored on a non-transitory computer-readable medium, the NMR data of the target object; and
executing, by the computer, the instructions stored on the non-transitory computer-readable medium to analyse the received NMR data using a model of the diffusive behaviour of particles within the target object, wherein:
the model includes a time parameter and a space parameter, the time parameter describing temporal characteristics of the diffusive behaviour of particles in the model and the space parameter describing spatial characteristics of the diffusive behaviour of particles in the model;
the model is constrained such that the value of the time parameter and the value of the space parameter are related according to a correlation function; and
the model comprises a random walk model,
characterised in that:
a) the space parameter describes a size of steps made by the particles in the random walk model and the space parameter is an exponent relating to a probability density function of steps made by the particles in the random walk model; and/or b) the time parameter describes a time between steps made by the particles in the random walk model and the time parameter describes an exponent relating to a probability density function of time between steps made by the particles in the random walk model.

2. The method of claim 1, wherein the model comprises a continuous-time random walk model.

3. The method of claim 1, wherein the correlation function is such that the pairs of values of the time parameter and the space parameter satisfying the correlation function comprise a pair of values where the diffusive behaviour of the particles in the model obeys a Gaussian random walk.

4. The method of claim 3, wherein:
the pair of values where the diffusive behaviour of the particles in the model obeys a Gaussian random walk is given by $\alpha=1$ and $\beta=2$, and a variance of a displacement of the particles in the model is proportional to $$t^{\frac{2\alpha}{\beta}},$$

where $\alpha$ is the time parameter and $\beta$ is the space parameter.

5. The method of claim 4, wherein the correlation function is such that the values of the time parameter and the space parameter satisfying the correlation function further satisfy $|\beta-2\alpha|<0.5$ and $0\leq\alpha\leq1$ and $0\leq\beta\leq2$.

6. The method of claim 3, wherein the correlation function is such that the time parameter increases monotonically as a function of the space parameter.

7. The method of claim 6, wherein the correlation function is such that the time parameter is linearly related to the space parameter for at least a range of values of the time parameter.

8. The method of claim 7, wherein the correlation function is such that the time parameter is directly proportional to the space parameter.

9. The method of claim 8, wherein the correlation function is such that $2\alpha=\beta$, wherein $\alpha$ is the time parameter and $\beta$ is the space parameter.

10. The method of claim 9, wherein the step of analysing the NMR data comprises:
calculating a diffusion spectrum for each of one or more regions of the target object, the diffusion spectrum of a region being a probability density function for values of a diffusion parameter characterising the diffusive behaviour of particles within the region.

11. The method of claim 10, wherein the diffusion parameter is one of an apparent diffusion coefficient and a length scale of a structure within the region of the target object.

12. The method of claim 1, wherein calculating the diffusion spectrum comprises taking an integral transform of the model of the diffusive behaviour of particles within the target object, wherein optionally the integral transform is a Laplace transform or a Fourier transform.

13. The method of claim 1, wherein the step of analysing the NMR data comprises:
calculating a three-dimensional representation of a structure within the target object on the basis of the model, the calculation using a variation in directionality of the diffusive behaviour of particles within the target object as a function of position within the target object; and producing output data based on the three-dimensional representation.

14. The method of claim 13, wherein the step of producing output data comprises:
applying a tractography algorithm to determine the orientations of elements of the structure within the target object.

15. The method of claim 13, further comprising determining, on the basis of the output data, information about a microstructure within the target object.

16. The method of claim 15, further comprising identifying, on the basis of the information about the microstructure, a structure type of a target region containing the microstructure.

17. The method of claim 16, wherein the target object is a human or animal subject, and the identified structure type is associated with a set of one or more pathologies.

18. The method of claim 17, wherein the set of pathologies includes one or more of dementia, or dementia-related tissue damage; a presence of a tumour; a grade of a tumour; a malignancy of a tumour; a presence of tissue damage due to stroke; a presence of stroke lesions; and/or a likelihood of tissue damage due to stroke.

19. The method of claim 1, wherein receiving the NMR data comprises receiving NMR diffusion signal attenuation data.

20. A non-transitory computer-readable medium comprising instructions which, when executed by a computer, cause the computer to carry out the method of claim 1.

21. An apparatus comprising:
a magnetic resonance scanner configured to generate nuclear magnetic resonance, NMR, data of a target object; and
a computer configured to receive the NMR data associated with the target object, and execute instructions stored on a non-transitory computer-readable medium, the instructions stored on the non-transitory computer readable medium configured to cause the computer to analyse the NMR data using a model of the diffusive behaviour of particles within the target object, wherein:
the model includes a time parameter and a space parameter, the time parameter describing temporal characteristics of the diffusive behaviour of particles in the model and the space parameter describing spatial characteristics of the diffusive behaviour of particles in the model;
the model is constrained such that the value of the time parameter and the value of the space parameter are related according to a correlation function; and
the model comprises a random walk model,
characterised in that:
a) the space parameter describes a size of steps made by the particles in the random walk model and the space parameter is an exponent relating to a probability density function of steps made by the particles in the random walk model; and/or
b) the time parameter describes a time between steps made by the particles in the random walk model and the time parameter describes an exponent relating to a probability density function of time between steps made by the particles in the random walk model.

* * * * *